US010799345B2

(12) United States Patent
Hariton et al.

(10) Patent No.: US 10,799,345 B2
(45) Date of Patent: Oct. 13, 2020

(54) PROSTHETIC VALVE WITH PROTECTIVE FABRIC COVERING AROUND TISSUE ANCHOR BASES

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CardioValve Ltd., Or Yehuda (IL)

( * ) Notice: Subject to any disclaimer, the term of this patent is extended or adjusted under 35 U.S.C. 154(b) by 105 days.

(21) Appl. No.: 16/135,843

(22) Filed: Sep. 19, 2018

(65) Prior Publication Data

US 2019/0083247 A1 Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2418* (2013.01); *A61F 2/243* (2013.01); *A61F 2/2436* (2013.01); *A61F 2/2445* (2013.01); *A61F 2/2454* (2013.01); *A61F 2/2463* (2013.01); *A61F 2/246* (2013.01); *A61F 2/2409* (2013.01); *A61F 2/2466* (2013.01); *A61F 2210/0014* (2013.01); *A61F 2220/0008* (2013.01); *A61F 2250/007* (2013.01)

(58) Field of Classification Search
CPC ......... A61F 2/2412; A61F 2/2418; A61F 2/24
See application file for complete search history.

(56) References Cited

U.S. PATENT DOCUMENTS

| 5,776,140 A | 7/1998 | Cottone |
| 5,957,949 A | 9/1999 | Leonhardt et al. |
| 6,010,530 A | 1/2000 | Goicoechea |
| 6,402,780 B2 | 6/2002 | Williamson, IV et al. |

(Continued)

FOREIGN PATENT DOCUMENTS

| EP | 1264582 A2 | 12/2002 |
| WO | WO 2008/029296 A2 | 3/2008 |

(Continued)

OTHER PUBLICATIONS

International Search Report dated Dec. 5, 2011, by the United States Patent and Trademark Office in PCT/IL2011/000582 (3 pages).

(Continued)

*Primary Examiner* — Jason-Dennis N Stewart
(74) *Attorney, Agent, or Firm* — Finnegan, Henderson, Farabow, Garrett & Dunner, LLP

(57) ABSTRACT

A prosthetic valve for implantation within a native mitral valve may be provided. The prosthetic valve may include an annular valve body. The prosthetic valve may also include a plurality of tissue anchors arranged about the valve body and configured to extend from connection points on the valve body. The prosthetic valve may also include at least one protective fabric covering extending over each of the connection points between each tissue anchor and the valve body.

17 Claims, 21 Drawing Sheets

(56) References Cited

U.S. PATENT DOCUMENTS

| | | |
|---|---|---|
| 6,458,153 B1 | 10/2002 | Bailey et al. |
| 6,669,724 B2 | 12/2003 | Park et al. |
| 6,733,525 B2 | 5/2004 | Yang et al. |
| 7,201,772 B2 | 4/2007 | Schwammenthal et al. |
| 7,442,204 B2 | 10/2008 | Schwammenthal et al. |
| 7,837,727 B2 | 11/2010 | Goetz et al. |
| 7,959,672 B2 | 6/2011 | Salahieh et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,579,964 B2 | 11/2013 | Lane et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Hacohen et al. |
| 8,998,982 B2 | 4/2015 | Richter et al. |
| 9,017,399 B2 | 4/2015 | Hacohen et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,072,603 B2 | 7/2015 | Tuval et al. |
| 9,095,434 B2 | 8/2015 | Rowe |
| 9,125,740 B2 | 9/2015 | Morriss et al. |
| 9,132,009 B2 | 9/2015 | Hacohen et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,295,552 B2 | 3/2016 | McLean et al. |
| D755,384 S | 5/2016 | Pesce et al. |
| 9,345,573 B2 | 5/2016 | Nyuli et al. |
| 9,387,078 B2 | 7/2016 | Gross et al. |
| 9,439,757 B2 | 9/2016 | Wallace et al. |
| 9,445,893 B2 | 9/2016 | Vaturi |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| D800,908 S | 10/2017 | Hariton et al. |
| 9,788,941 B2 | 10/2017 | Hacohen |
| 9,974,651 B2 | 5/2018 | Hariton et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,321,995 B1 | 6/2019 | Christianson et al. |
| 10,327,895 B2 | 6/2019 | Lozonschi et al. |
| 10,357,360 B2 | 7/2019 | Hariton et al. |
| 10,376,361 B2 | 8/2019 | Gross et al. |
| 10,390,952 B2 | 8/2019 | Hariton et al. |
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 2004/0186558 A1 | 9/2004 | Pavcnik et al. |
| 2004/0210304 A1 | 10/2004 | Seguin et al. |
| 2004/0249433 A1 | 12/2004 | Freitag |
| 2005/0137697 A1 | 6/2005 | Salahieh et al. |
| 2005/0240200 A1 | 10/2005 | Bergheim |
| 2006/0004469 A1 | 1/2006 | Sokel |
| 2006/0020327 A1 | 1/2006 | Lashinski et al. |
| 2006/0052867 A1 | 3/2006 | Revuelta et al. |
| 2006/0259137 A1 | 11/2006 | Artof et al. |
| 2007/0056346 A1 | 3/2007 | Spenser et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keränen et al. |
| 2011/0004299 A1 | 1/2011 | Navia et al. |
| 2011/0029072 A1 | 2/2011 | Gabbay |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0313515 A1 | 12/2011 | Quadri et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0101571 A1 | 4/2012 | Thambar et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0144381 A1 | 6/2013 | Quadri et al. |
| 2013/0190861 A1 | 7/2013 | Chau et al. |
| 2013/0261738 A1 | 10/2013 | Clague et al. |
| 2013/0304200 A1 | 11/2013 | McLean et al. |
| 2014/0000112 A1 | 1/2014 | Braido et al. |
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |

(56) References Cited

U.S. PATENT DOCUMENTS

| | | |
|---|---|---|
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358224 A1* | 12/2014 | Tegels .................. A61L 27/34 623/2.14 |
| 2015/0018944 A1 | 1/2015 | O'Connell et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0320556 A1 | 11/2015 | Levi et al. |
| 2015/0327994 A1 | 11/2015 | Morriss et al. |
| 2015/0328000 A1* | 11/2015 | Ratz .................. A61F 2/2418 623/2.37 |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0184098 A1 | 6/2016 | Vaturi |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0209264 A1 | 7/2017 | Chau et al. |
| 2017/0231759 A1 | 8/2017 | Geist et al. |
| 2017/0231766 A1 | 8/2017 | Hariton et al. |
| 2017/0333187 A1 | 11/2017 | Hariton et al. |
| 2017/0367823 A1 | 12/2017 | Hariton et al. |
| 2018/0021129 A1 | 1/2018 | Peterson et al. |
| 2018/0049873 A1 | 2/2018 | Manash et al. |
| 2018/0055630 A1 | 3/2018 | Patel et al. |
| 2018/0153689 A1 | 6/2018 | Maimon et al. |
| 2018/0206983 A1 | 7/2018 | Noe et al. |
| 2018/0250126 A1 | 9/2018 | O'Connor et al. |
| 2018/0250130 A1 | 9/2018 | Hariton et al. |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0328519 A1 | 10/2019 | Hariton et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000579 A1 | 1/2020 | Manash et al. |
| 2020/0015964 A1 | 1/2020 | Noe et al. |
| 2020/0046497 A1 | 2/2020 | Hariton et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0129294 A1 | 4/2020 | Hariton et al. |

FOREIGN PATENT DOCUMENTS

| | | |
|---|---|---|
| WO | WO 2010/006627 A1 | 1/2010 |
| WO | WO 2010/057262 A1 | 5/2010 |
| WO | WO 2012/011108 A2 | 1/2012 |
| WO | WO 2012/036740 A2 | 3/2012 |
| WO | WO 2012/048035 A2 | 4/2012 |
| WO | WO 2013/059747 A1 | 4/2013 |
| WO | WO 2013/072496 A1 | 5/2013 |
| WO | WO 2013/078497 A1 | 6/2013 |
| WO | WO 2013/175468 A2 | 11/2013 |
| WO | WO 2014/115149 A2 | 7/2014 |
| WO | WO 2014/164364 A1 | 10/2014 |
| WO | WO 2016/016899 A1 | 2/2016 |
| WO | WO 2016/098104 A2 | 6/2016 |
| WO | WO 201 6/1 251 6 | 8/2016 |
| WO | WO 2018/025260 A1 | 2/2018 |
| WO | WO 2018/025263 A2 | 2/2018 |
| WO | WO 2018/029680 A1 | 2/2018 |
| WO | WO 2018/039631 A1 | 3/2018 |
| WO | WO 2018/112429 A1 | 6/2018 |
| WO | WO 2018/118717 A1 | 6/2018 |
| WO | WO 2018/131042 A2 | 7/2018 |
| WO | WO 2018/131043 A1 | 7/2018 |
| WO | WO 2019/195860 A2 | 10/2019 |

OTHER PUBLICATIONS

International Search Report dated Mar. 27, 2018, by the European Patent Office in PCT/IL2017/050849 (5 pages).
International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).
Written Opinion of the International Searching Authority issued by the United States Patent and Trademark Office in PCT/IL2011/000582 (12 pages).
Written Opinion of the International Searching Authority issued by the European Patent Office in PCT/IL2017/050849 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).

(56) References Cited

OTHER PUBLICATIONS

Written Opinion of the International Searching Authority issued by the European Patent Office in PCT/IL2015/050792 (5 pages).
Written Opinion of the International Searching Authority issued by the European Patent Office in PCT/IL2017/050873 (12 pages).

\* cited by examiner

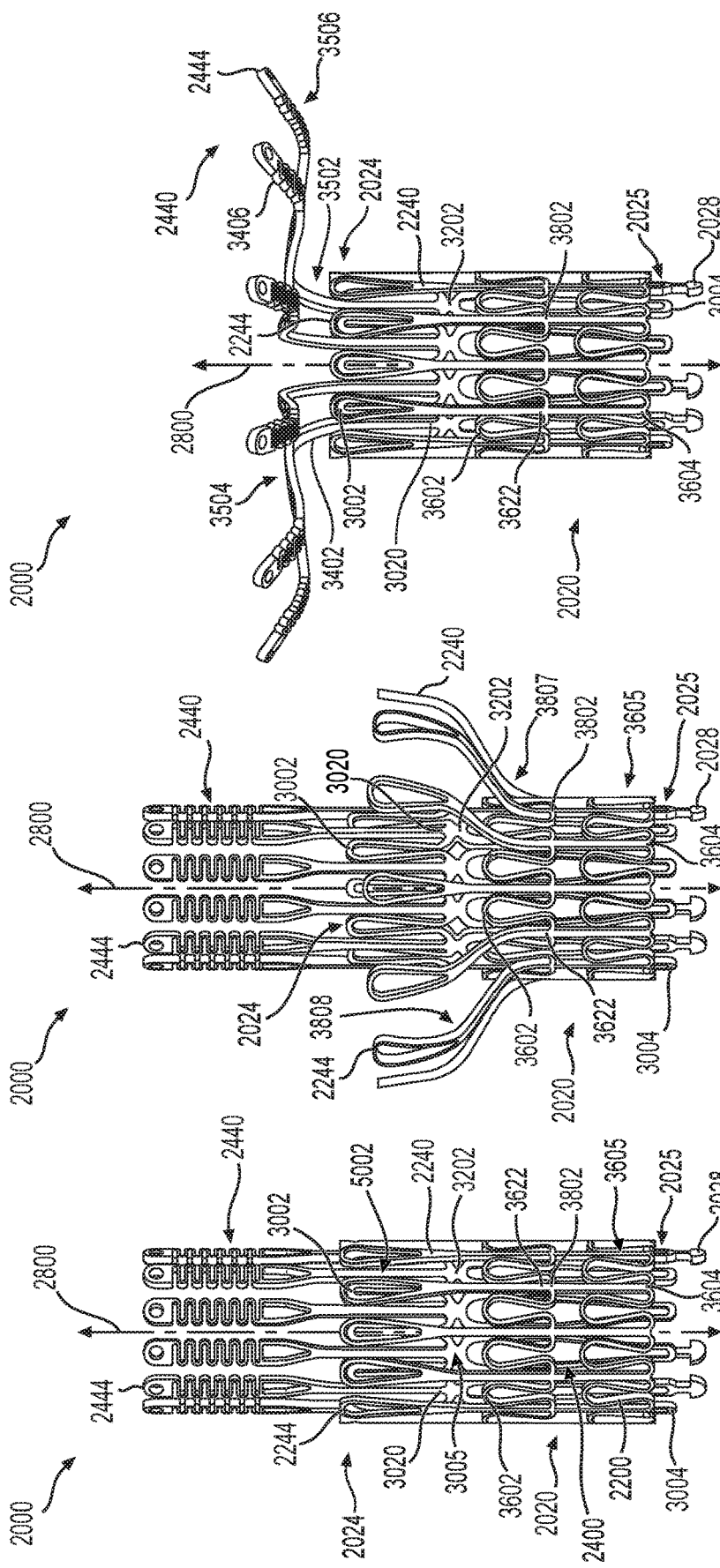

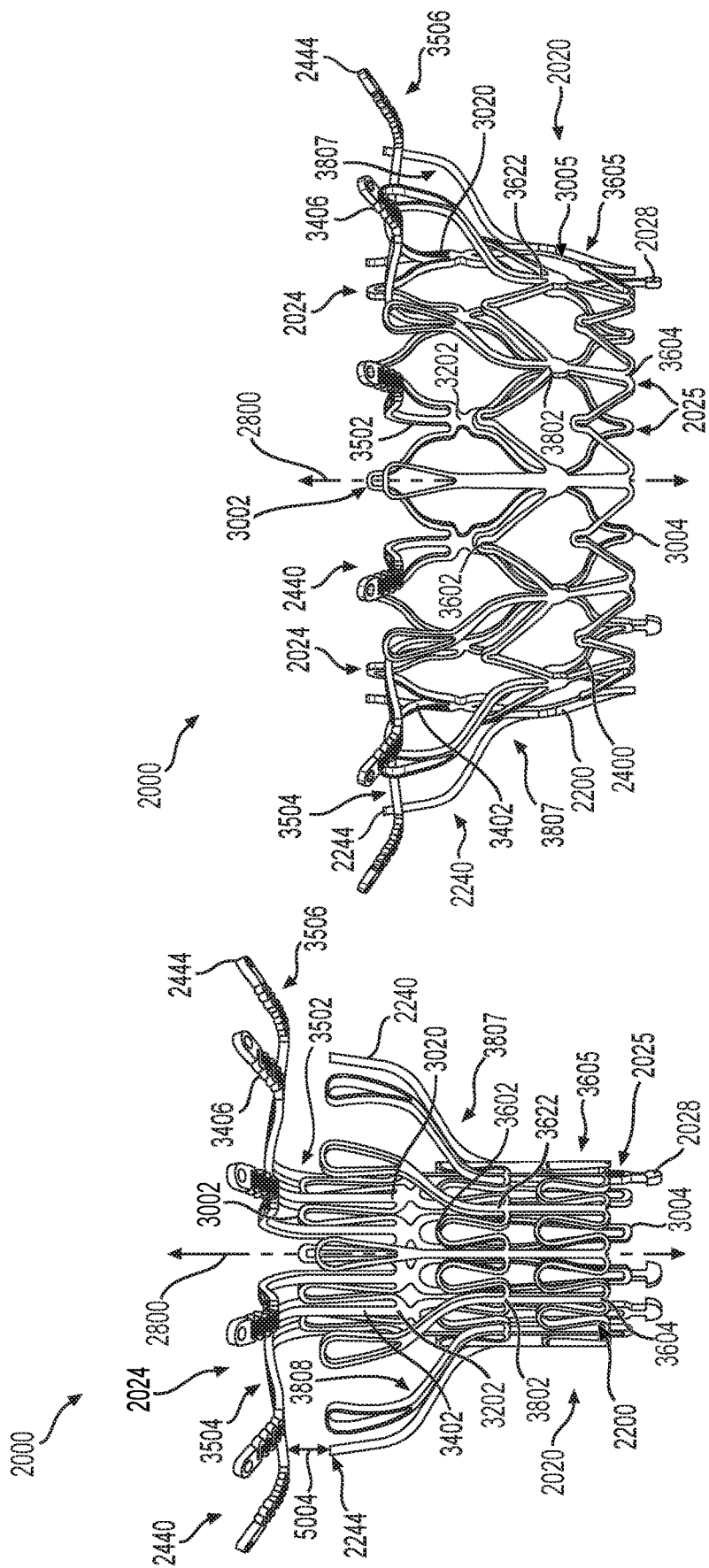

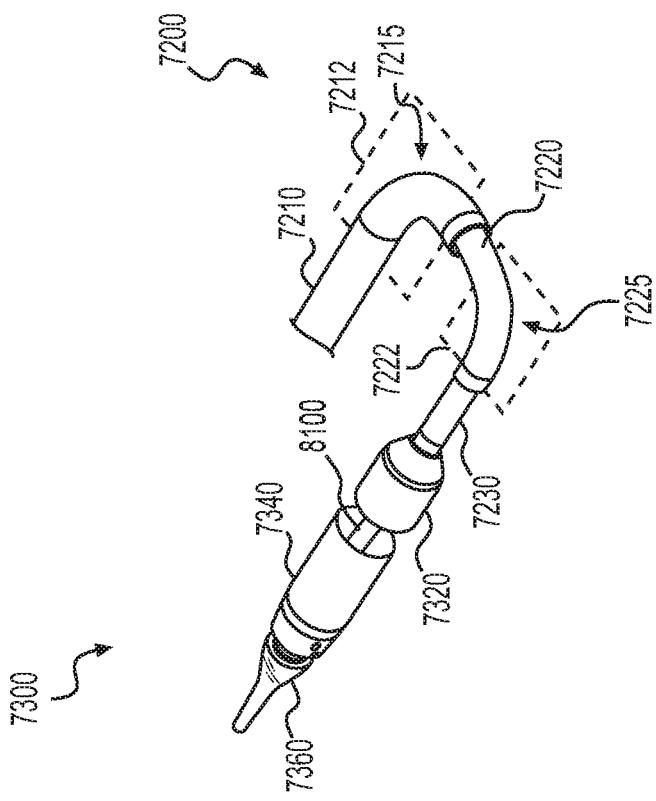
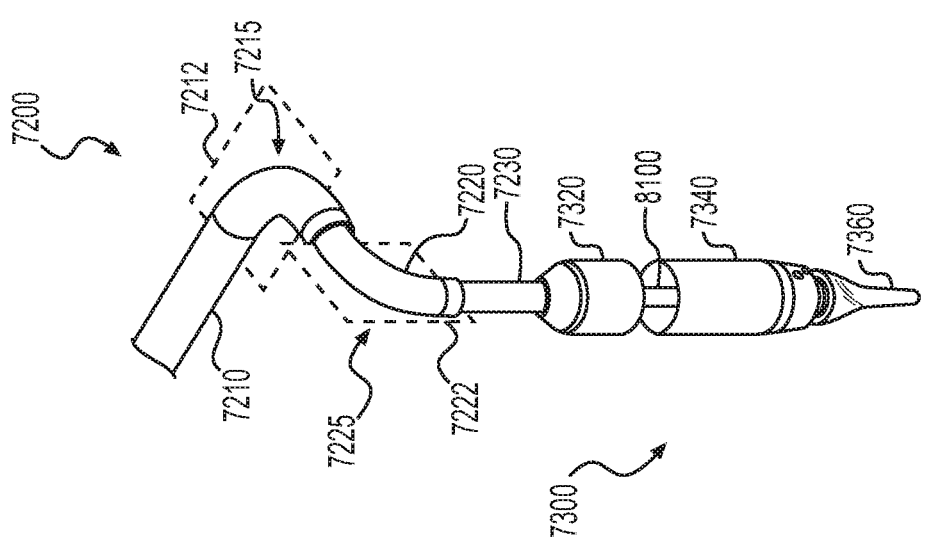

PROSTHETIC VALVE WITH PROTECTIVE FABRIC COVERING AROUND TISSUE ANCHOR BASES

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to prosthetic heart valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired due to, for example, cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size but that are still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit less protrusion into the chambers of the heart. The present disclosure also provides improved prosthetic heart valve delivery systems and methods of implanting prosthetic heart valves, such that prosthetic heart valves may be securely anchored at the implantation site.

SUMMARY

The present disclosure discloses prosthetic valves for implantation within a native mitral valve and methods for implanting prosthetic valves within a native mitral valve. Particular examples of the disclosure may pertain to a prosthetic valve formed at least partially of a valve body, a plurality of tissue anchors arranged about the valve body, and a protective fabric covering.

According to an exemplary embodiment of the present disclosure, a prosthetic valve for implantation within a native mitral valve is provided. The prosthetic valve includes an annular valve body. The prosthetic valve additionally includes a plurality of tissue anchors arranged about the valve body and configured to extend from connection points on the valve body. The prosthetic valve additionally includes at least one protective fabric covering extending over each of the connection points between each tissue anchor and the valve body.

Each connection point is covered by a separate protective fabric covering. Each of the at least one protective fabric covering covers less than half of a surface area of the corresponding tissue anchor. Each of the at least one protective fabric covering is arranged to expose a terminal end of the corresponding tissue anchor. The at least one protective fabric covering is at least partially constructed of PET. Stitching passes through the at least one protective fabric covering to secure the at least one protective fabric covering relative to the annular valve body. Stitching is configured to secure distinct portions of the at least one protective fabric covering together. Stitching is additionally configured to secure a portion of the at least one protective fabric covering to a skirt layer positioned beneath the at least one protective fabric covering. The at least one protective fabric covering is positioned over a liner which covers a majority of a surface area of one or more of the tissue anchors. At least two of the connection points are covered by separate protective fabric coverings that are substantially aligned in a common plane. The separate protective fabric coverings are substantially aligned in a common lateral plane. The at least one protective fabric covering is positioned in a radially outer direction relative to the annular valve body. The plurality of tissue anchors are configured to expand from a radially-contracted configuration to a radially-expanded configuration. The at least one protective fabric covering is arranged so that the at least one protective fabric covering does not impede movement of the plurality of tissue anchors from the radially-contracted configuration to the radially-expanded configuration. The at least one protective fabric covering includes a single strip of fabric wrapped about the at least one connection point. A terminal end of at least one tissue anchor is configured to be situated in an atrial direction relative to the at least one protective fabric covering. The prosthetic valve additionally includes a plurality of leaflets situated within the annular valve body. A point of connection of the plurality of leaflets to the annular valve body is situated in a ventricular direction relative to the at least one protective fabric covering. The tissue anchors are configured to engage ventricular tissue of a native heart valve. The prosthetic valve additionally includes a plurality of atrial tissue anchors configured to engage atrial tissue of the native heart valve. The annular valve body includes an annular outer frame and an inner frame situated at least partially within the annular outer frame. The ventricular tissue anchors extend from the annular outer frame and the atrial tissue anchors extend from the inner frame. The at least one protective fabric covering is positioned in a radially outer direction relative to the annular outer frame and relative to the inner frame. The at least one protective fabric covering is situated in a ventricular direction relative to the atrial tissue anchors. The at least one protective fabric covering is angularly offset from the atrial tissue anchors.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

FIG. 7C illustrates an exemplary configuration of a telescoping catheter assembly and the delivery capsule of the exemplary prosthetic valve delivery system of FIG. 7A, consistent with various embodiments of the present disclosure.

FIG. 7D illustrates another exemplary configuration of the telescoping catheter assembly and delivery capsule of FIG. 7C, consistent with various embodiments of the present disclosure.

DETAILED DESCRIPTION

Figure 1A:
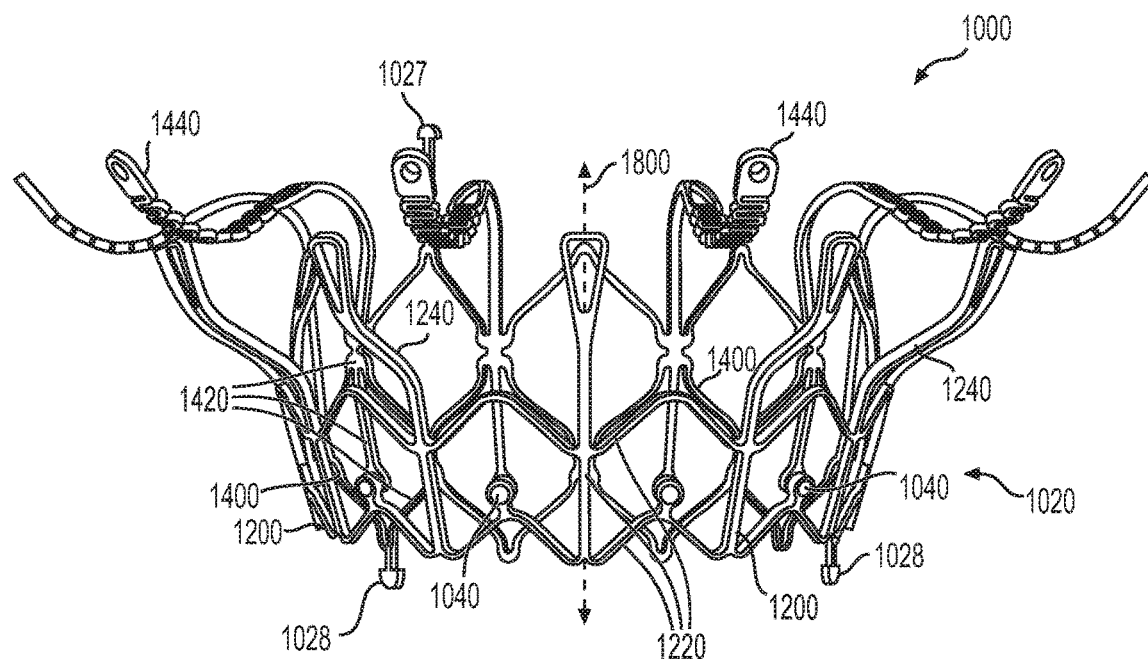
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
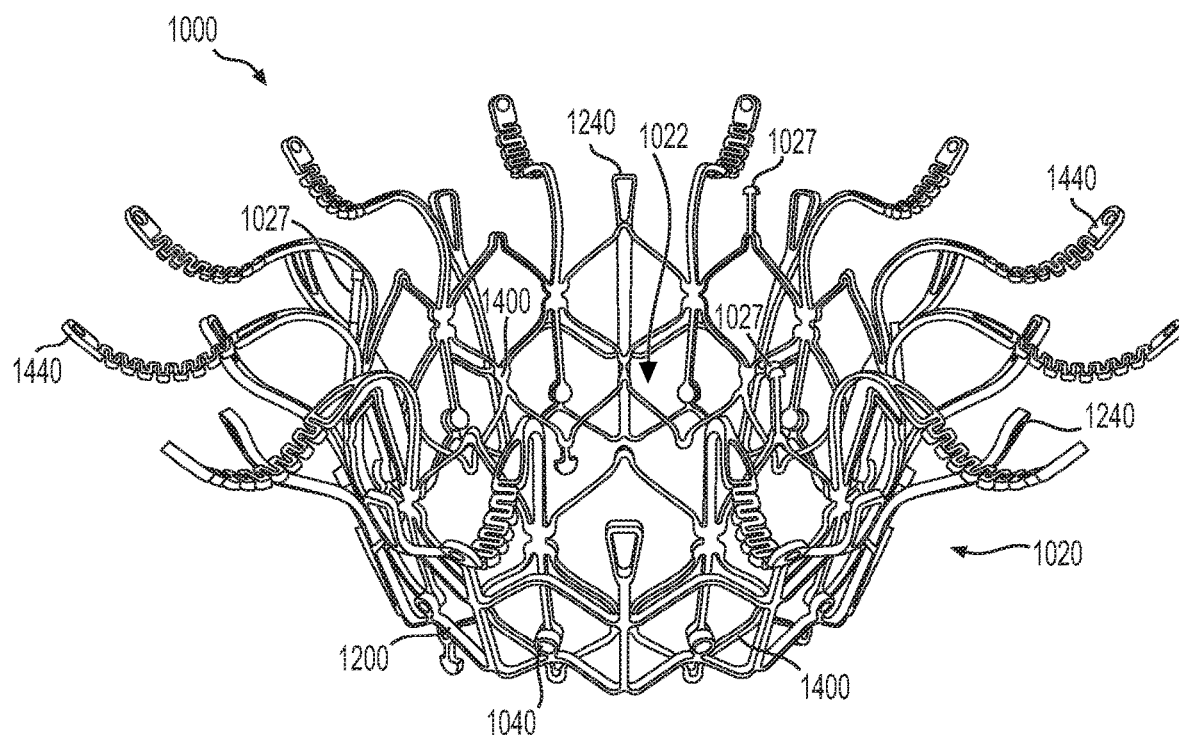
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
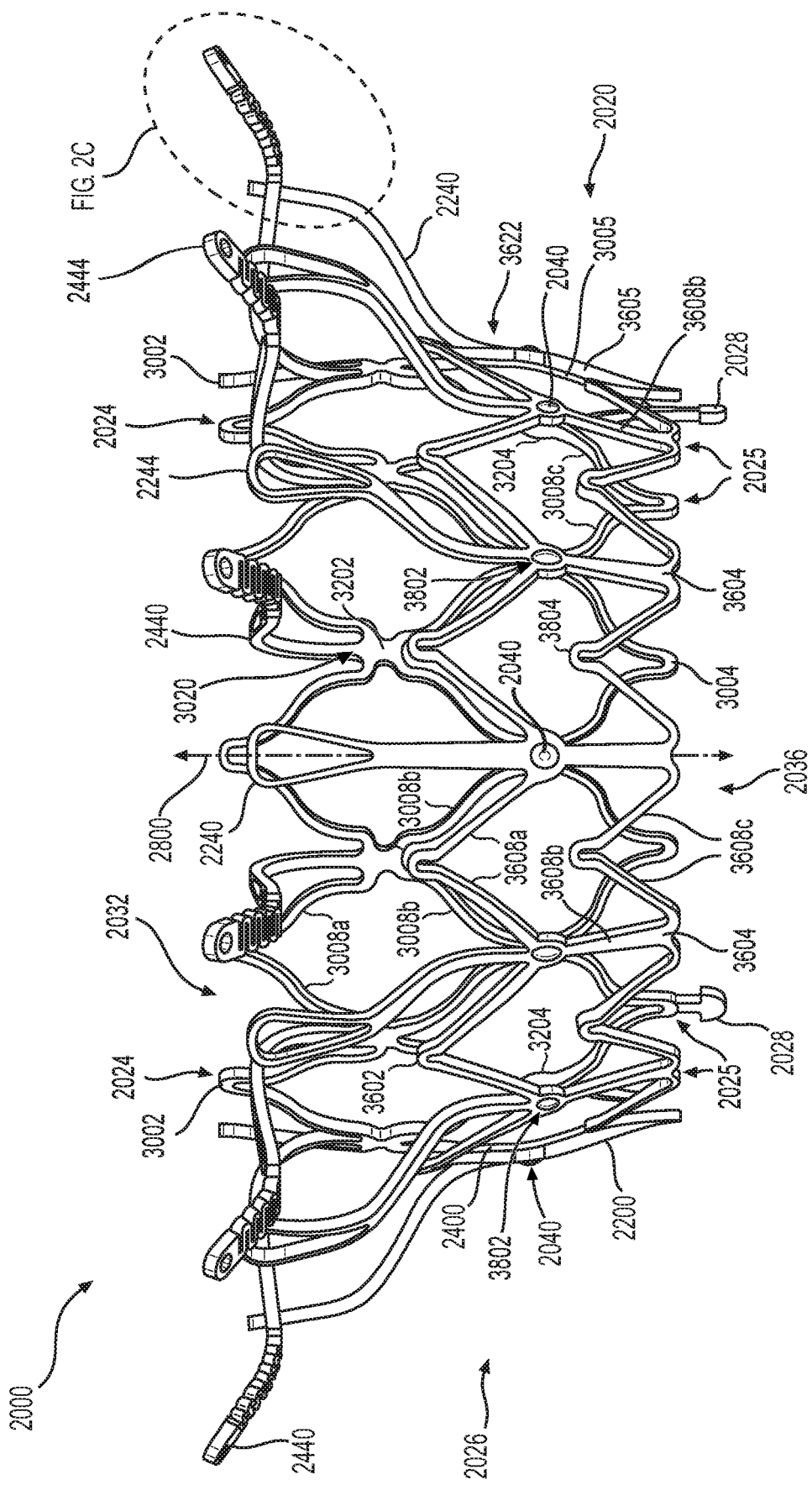
FIG. 2A illustrates a front elevation view of another exemplary frame for a prosthetic valve, consistent with various embodiments of the present disclosure.
Figure 2B:
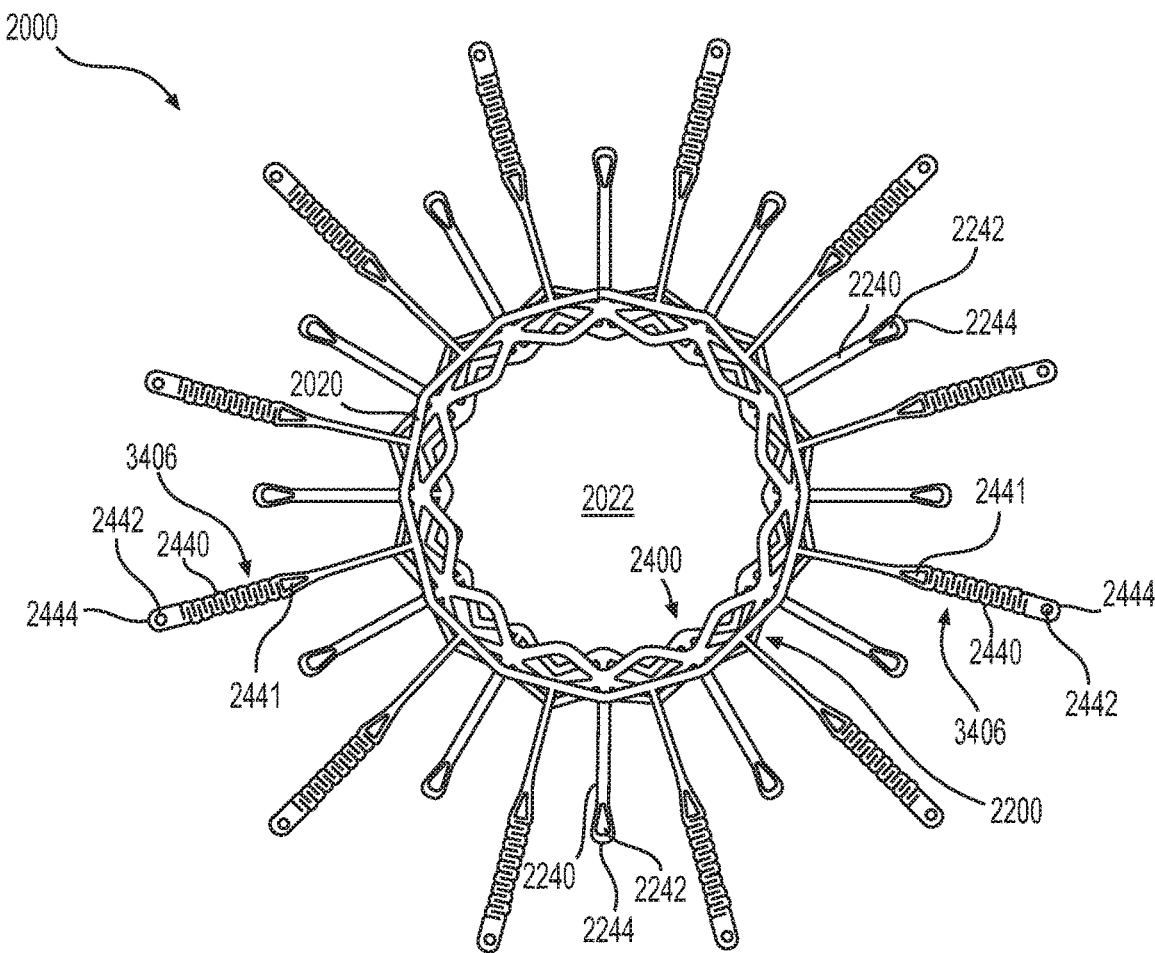
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrim, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
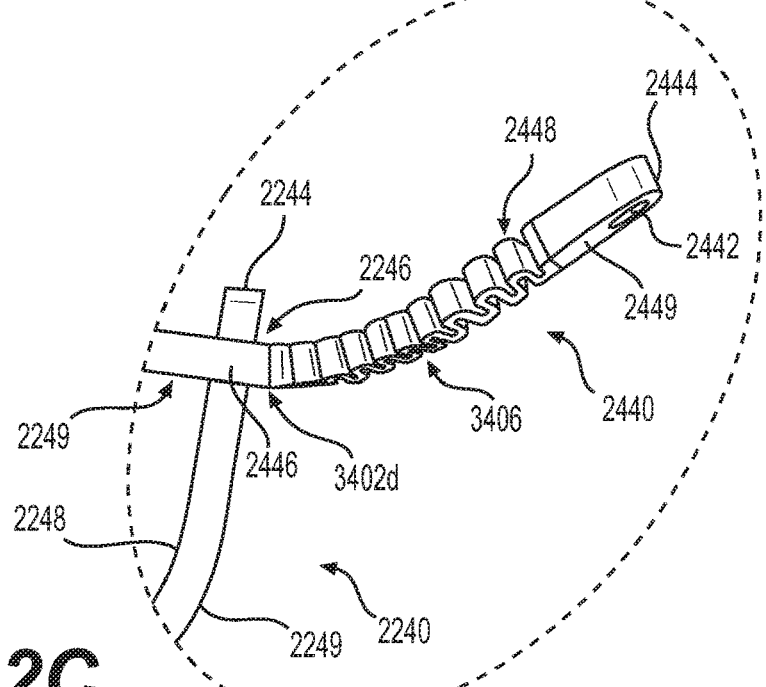
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
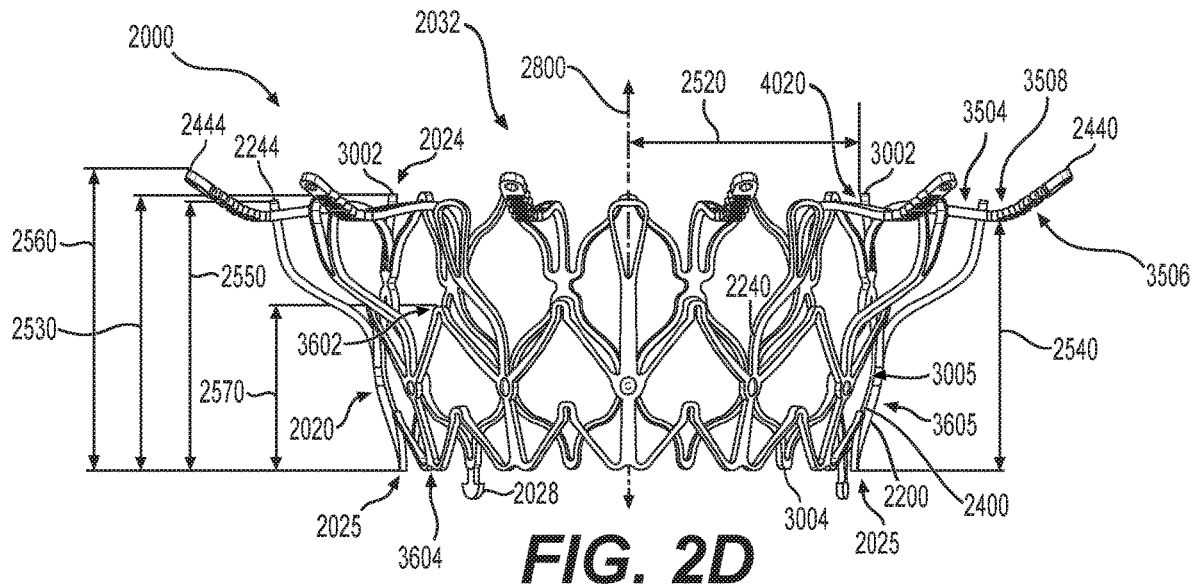
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
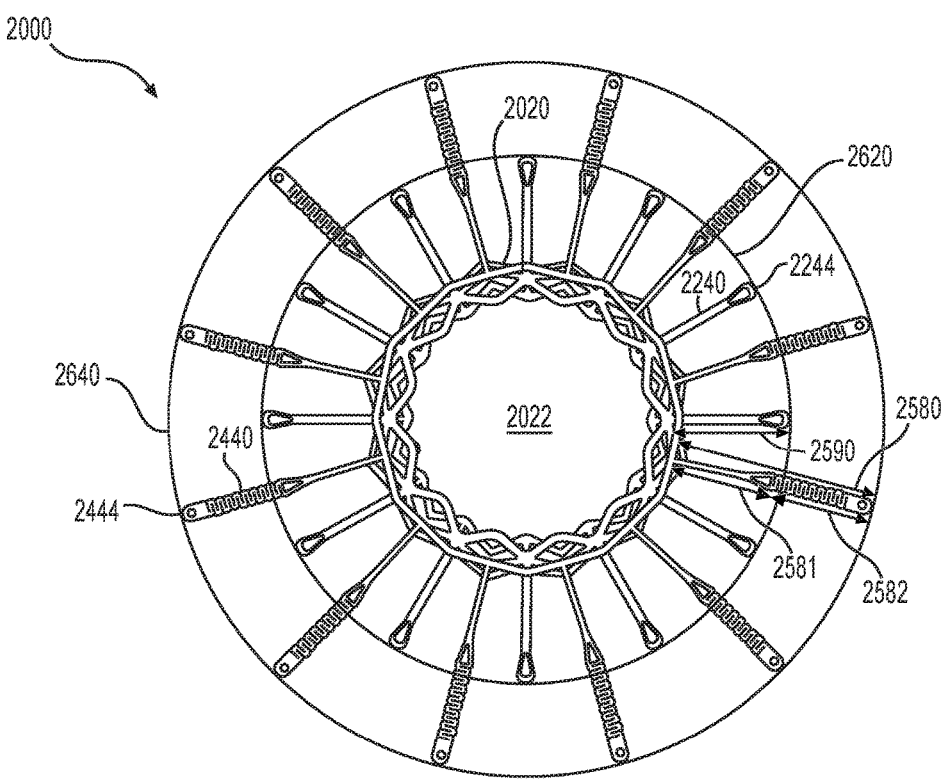
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
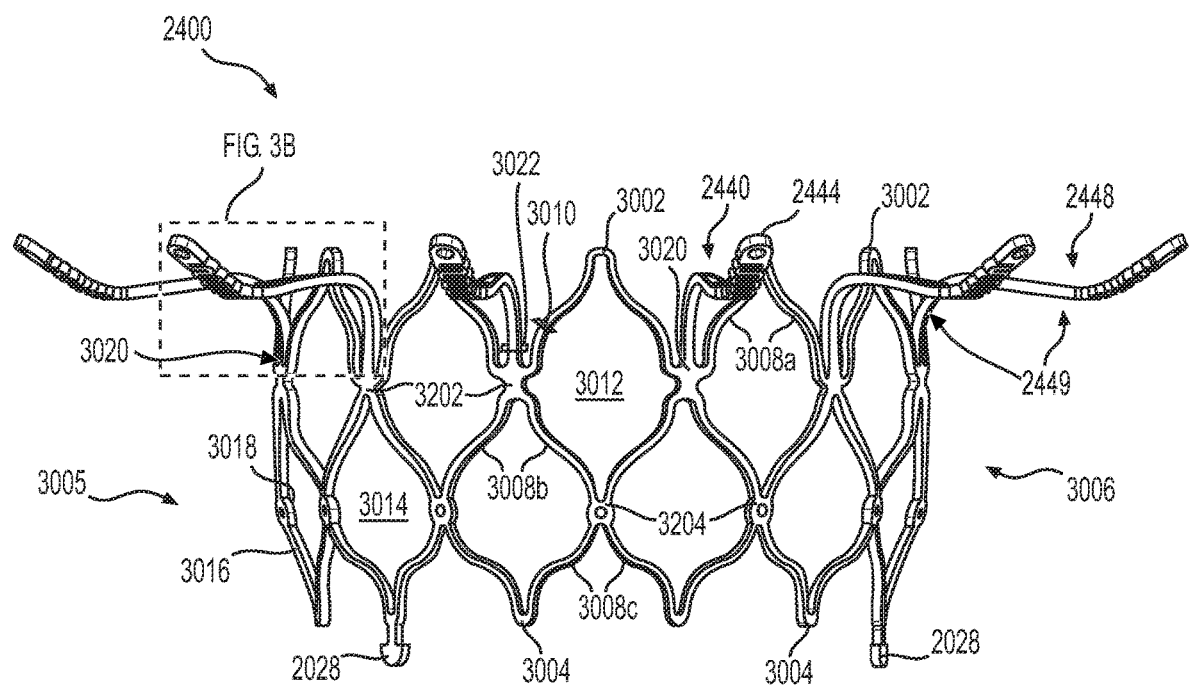
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
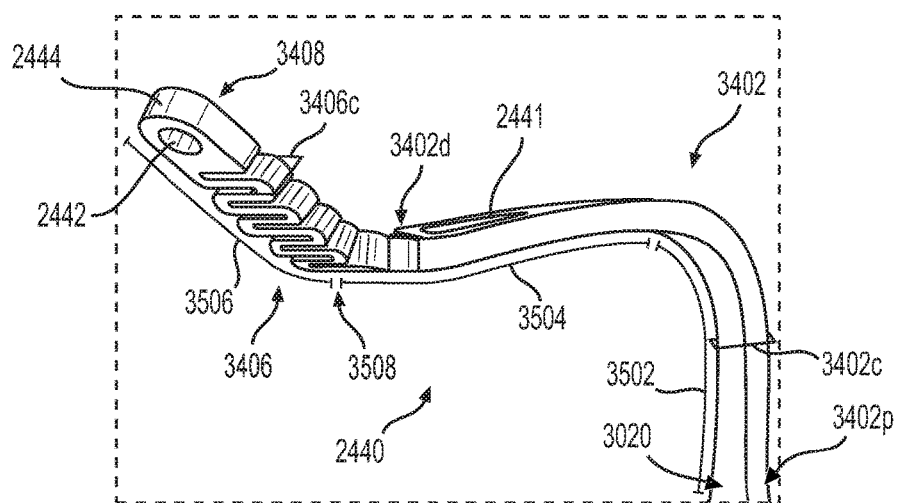
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
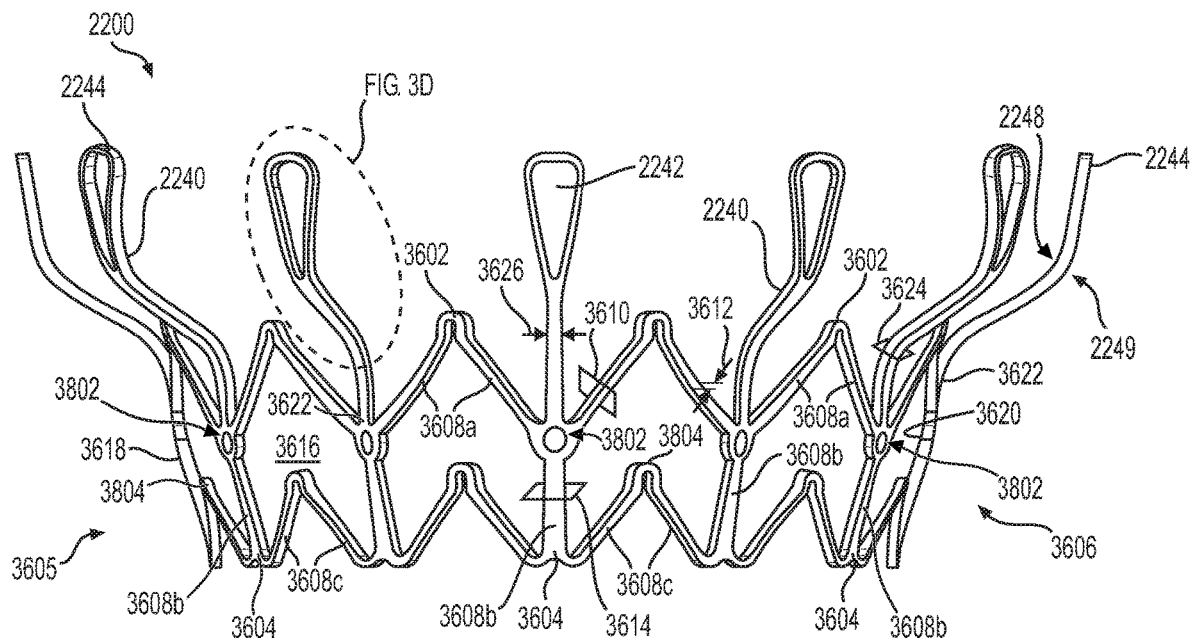
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
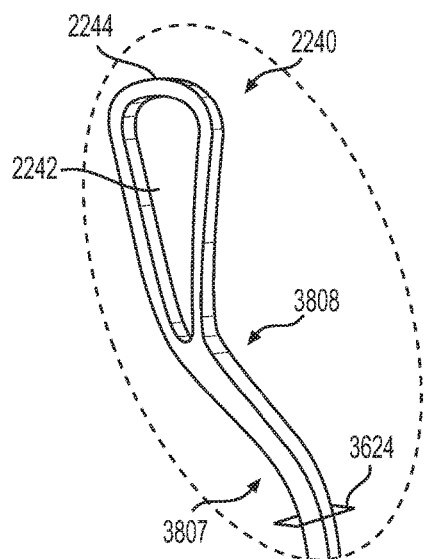
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
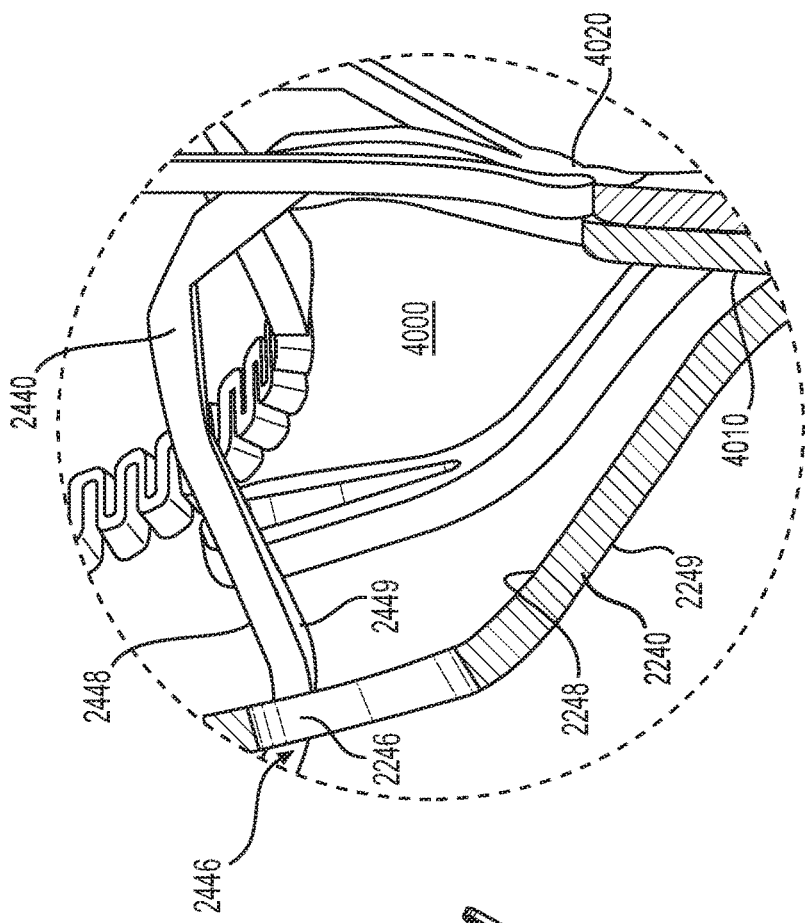
FIG. 4B illustrates an enlarged view of a volume between an atrial anchoring arm and a ventricular anchoring leg of the exemplary frame of FIG. 4A, consistent with various embodiments of the present disclosure.
Figure 4A:
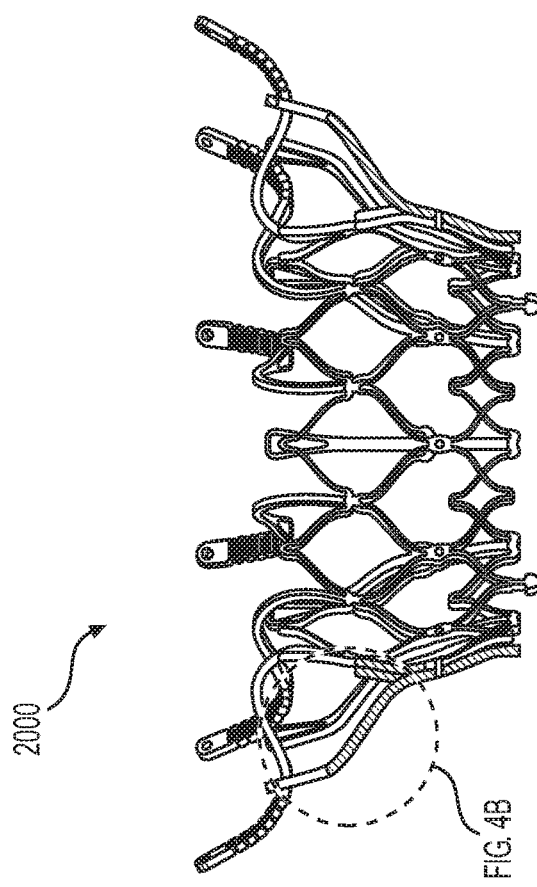
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
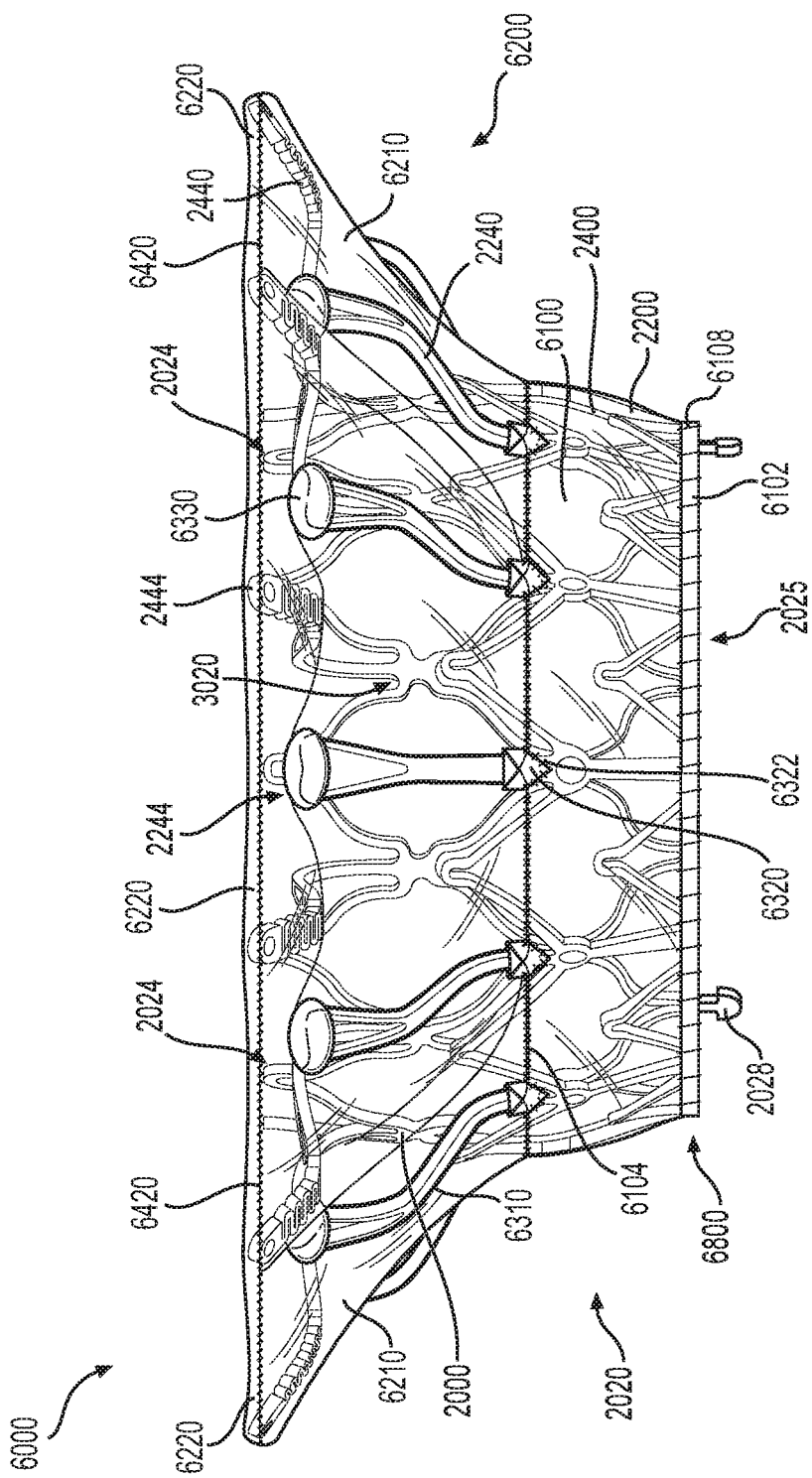
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
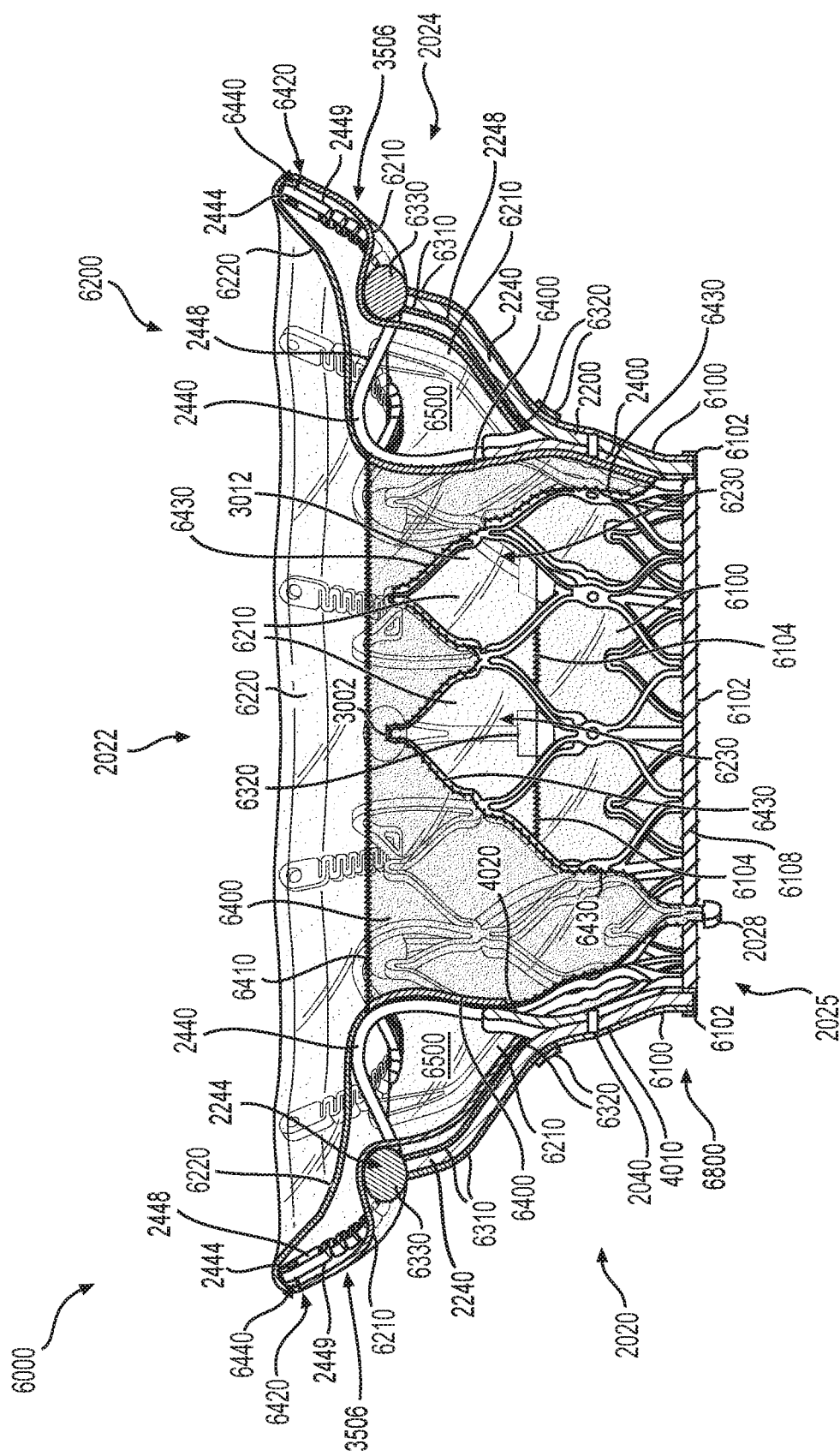
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
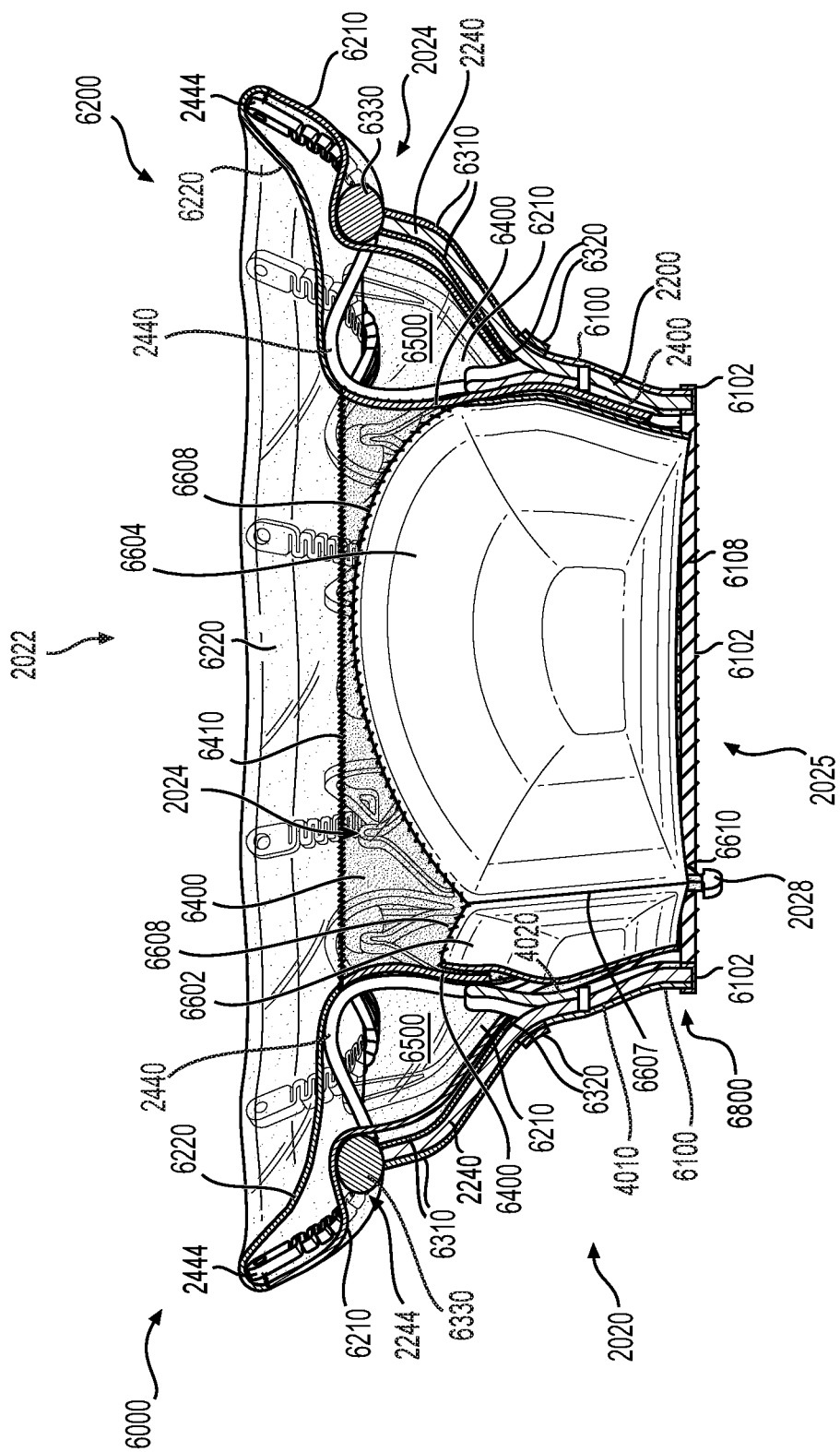
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
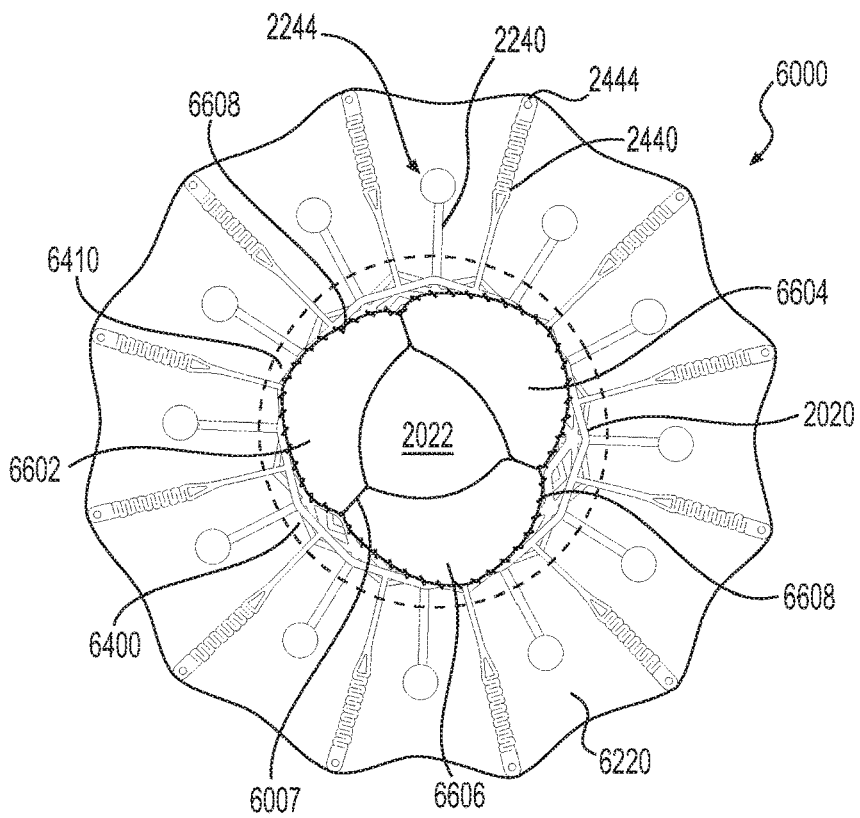
FIG. 6D illustrates a top plan view of the exemplary prosthetic valve of FIG. 6A with uninflated leaflets, consistent with various embodiments of the present disclosure.
Figure 6E:
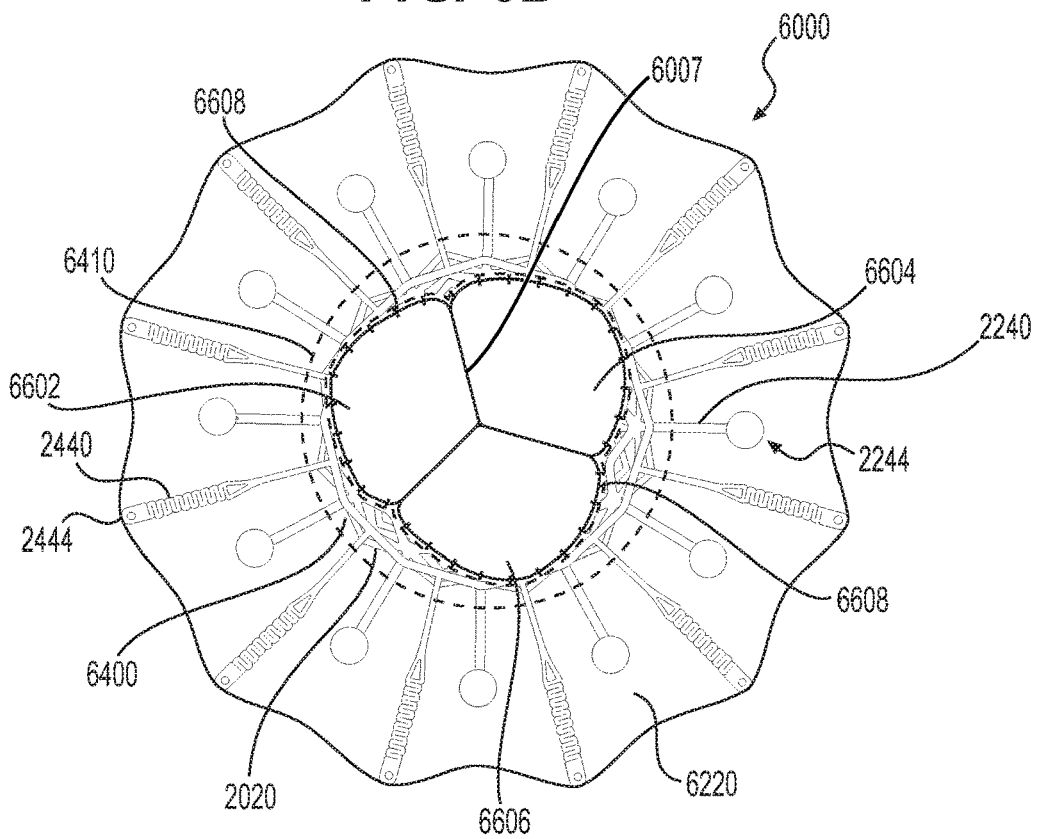
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
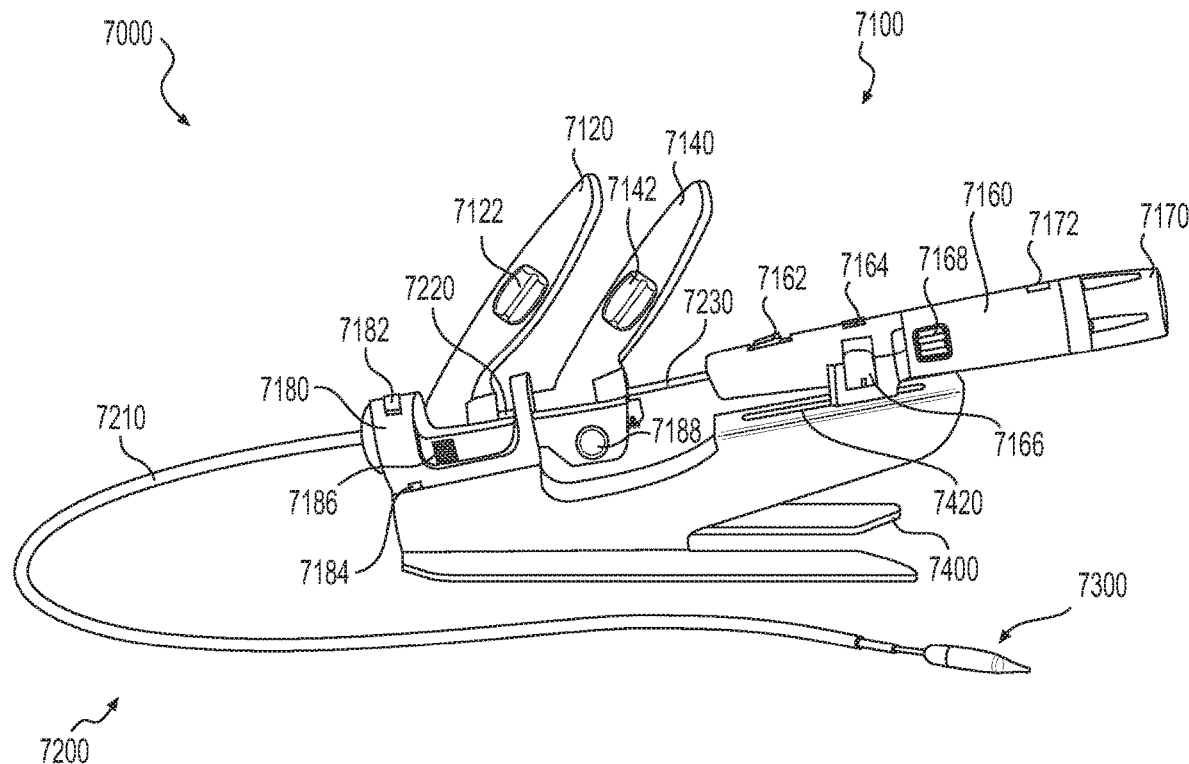
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
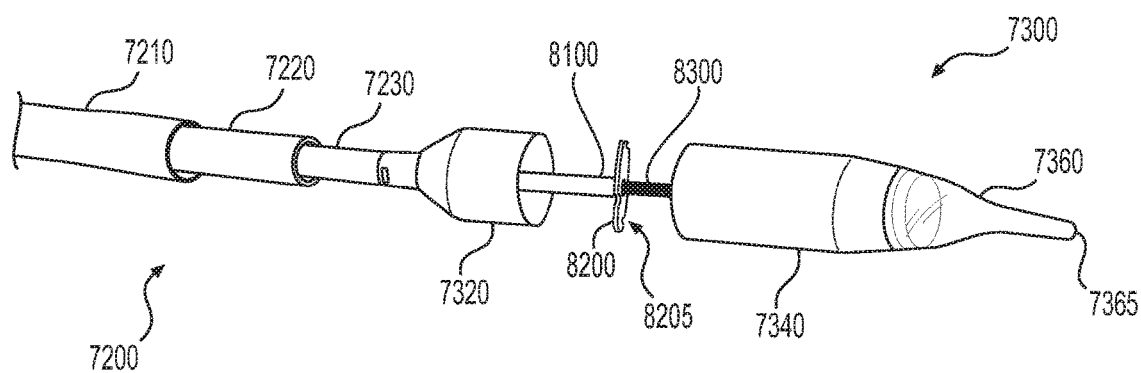
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
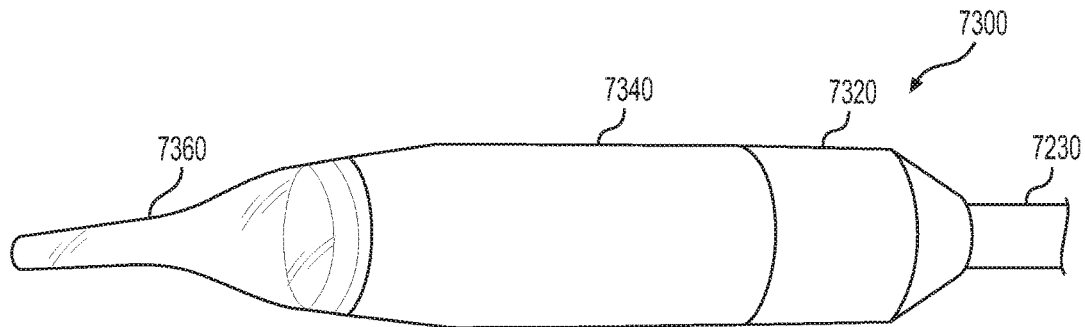
FIG. 8A illustrates another enlarged view of the exemplary delivery capsule of the prosthetic valve delivery system of FIG. 7A in a closed configuration, consistent with various embodiments of the present disclosure.
Figure 8B:
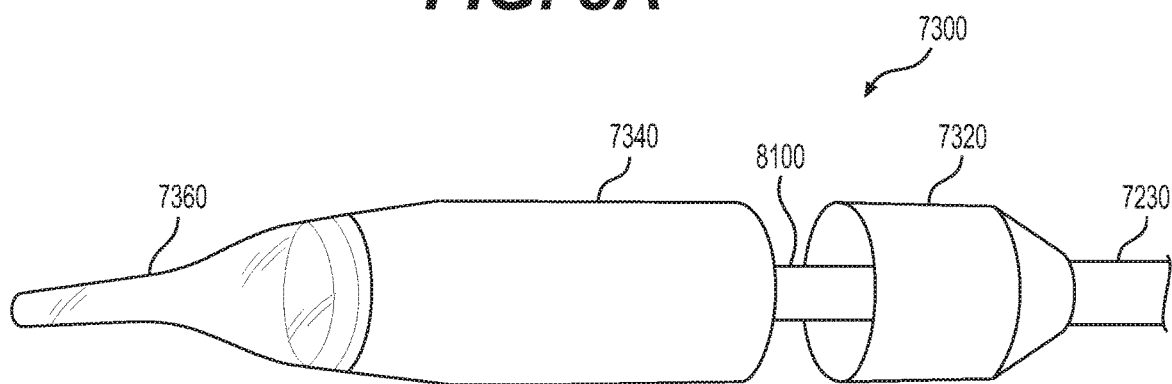
FIG. 8B illustrates the exemplary delivery capsule of FIG. 8A in an open configuration, consistent with various embodiments of the present disclosure.
Figure 8C:
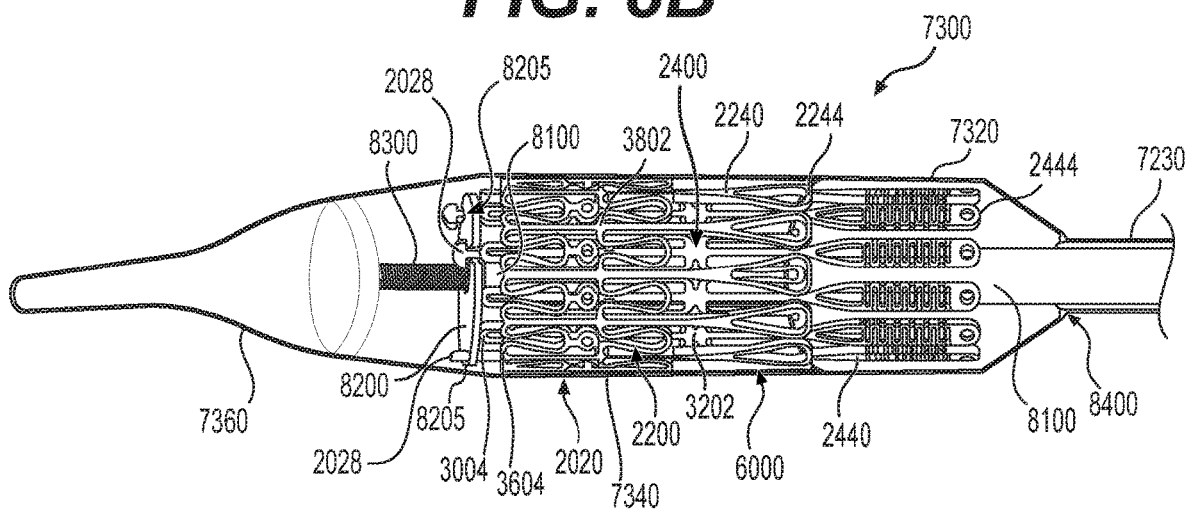
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
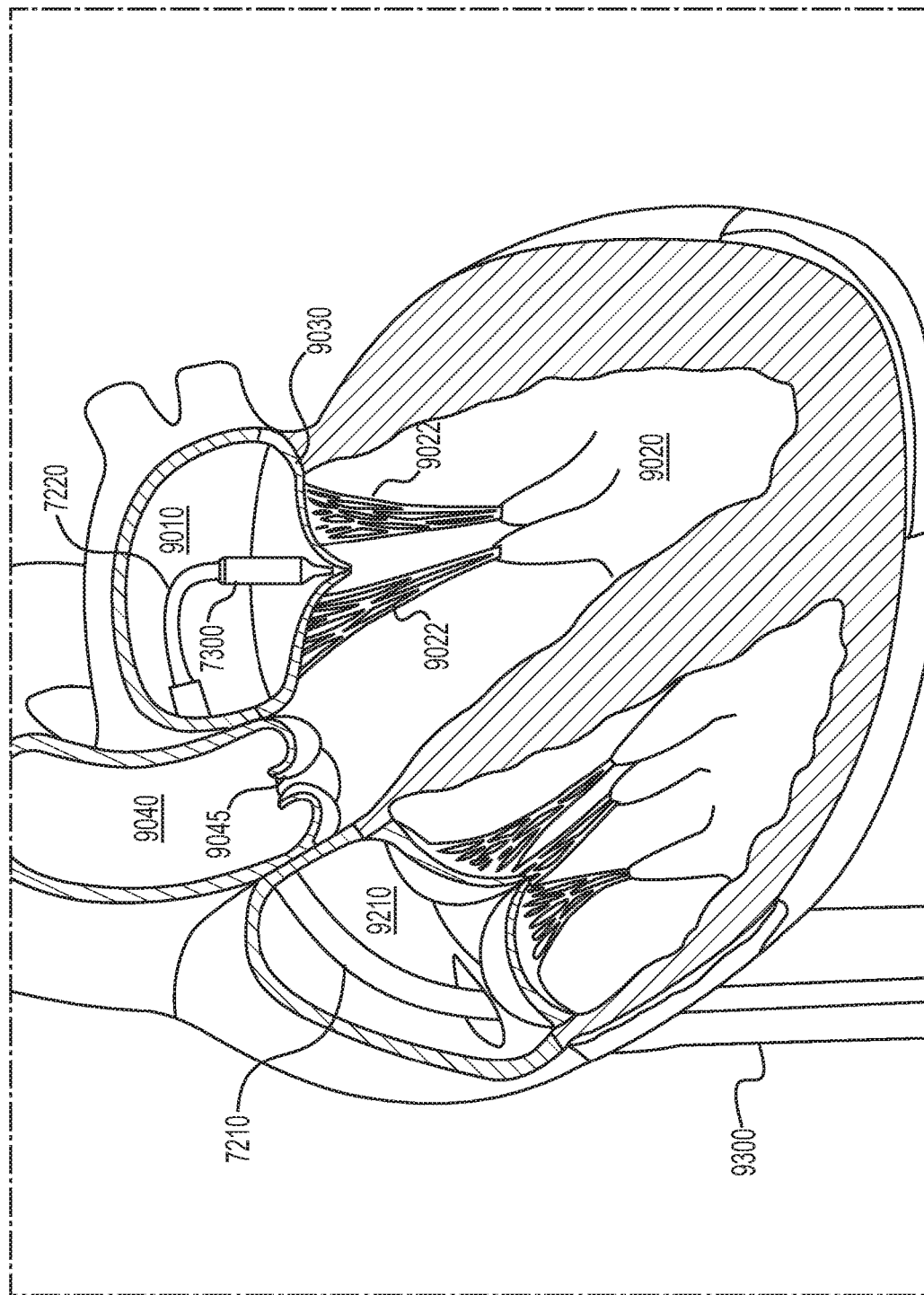
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10B:
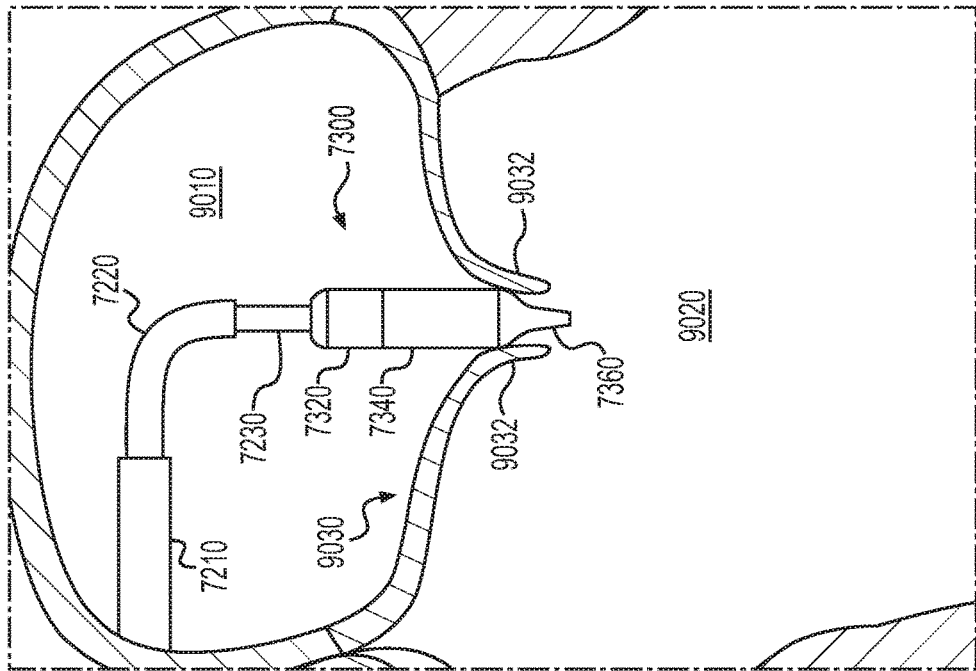
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10A:
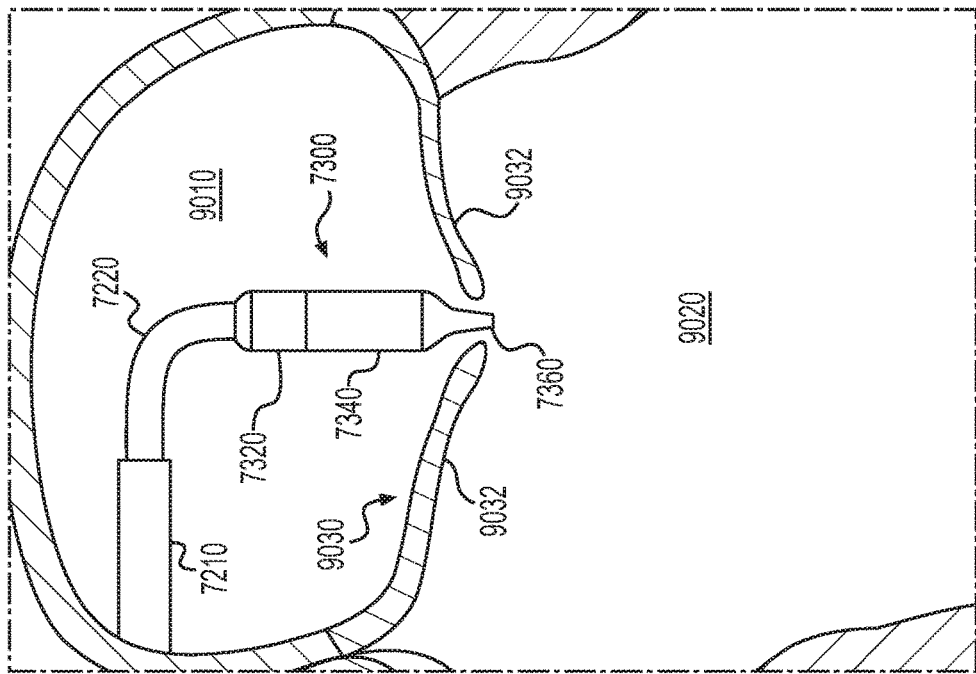
Figure 10D:
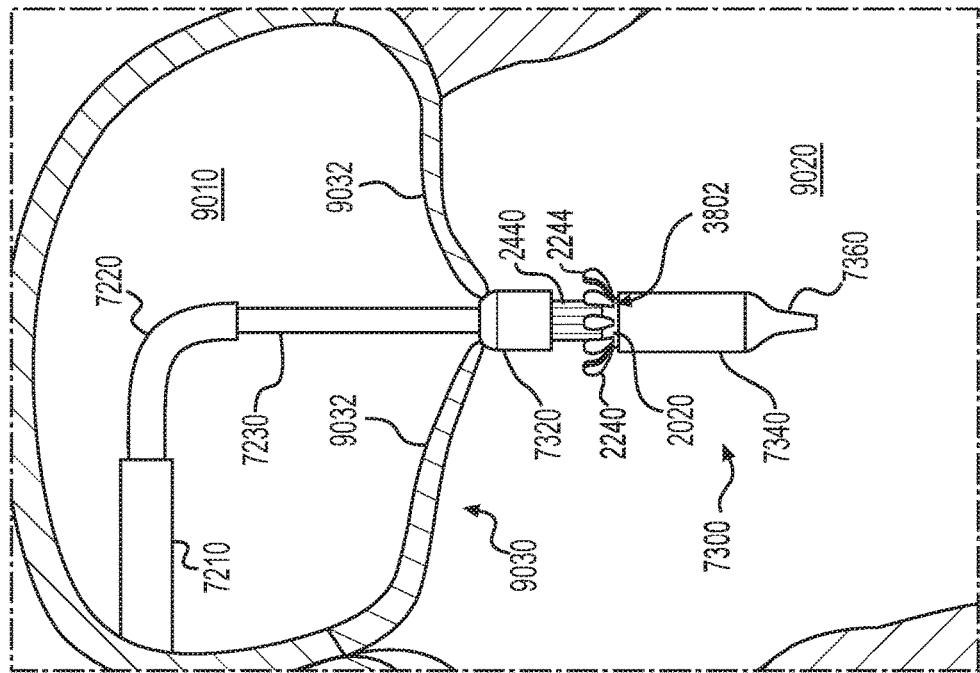
Figure 10C:
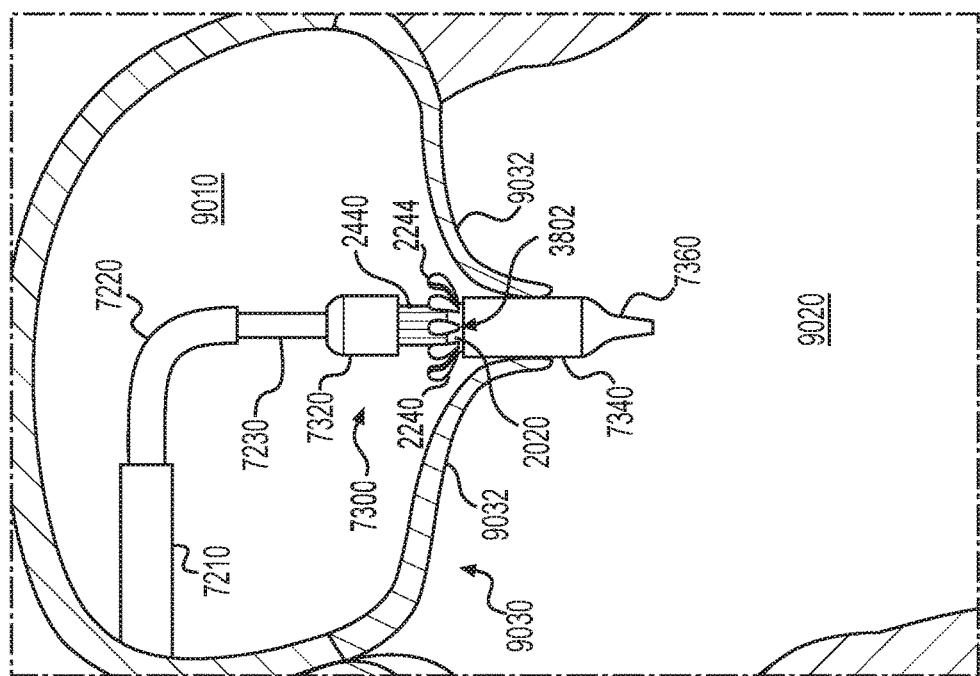

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
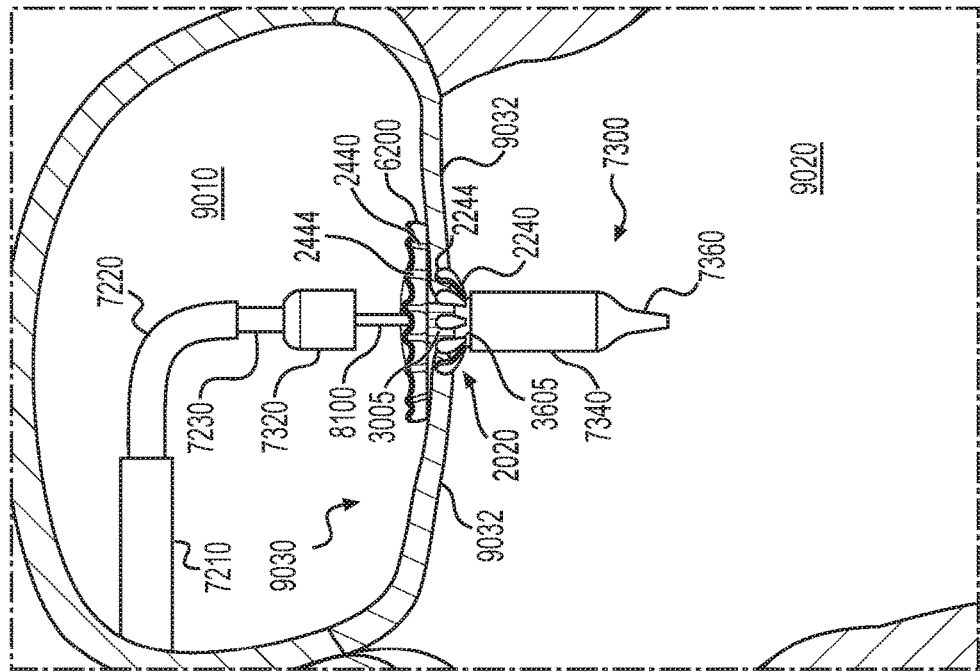
Figure 10E:
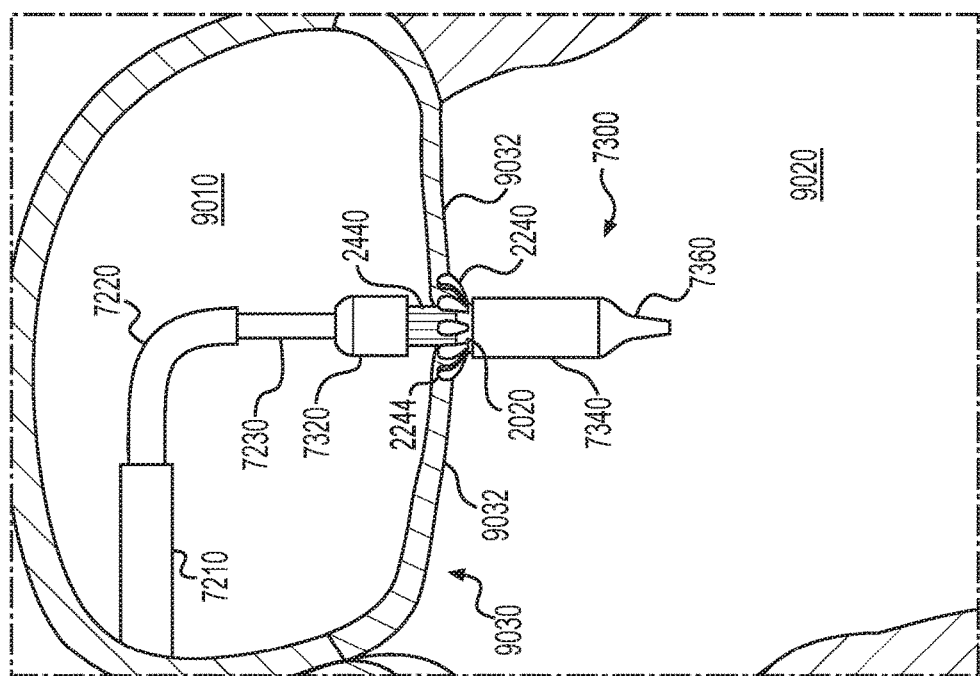

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10H:
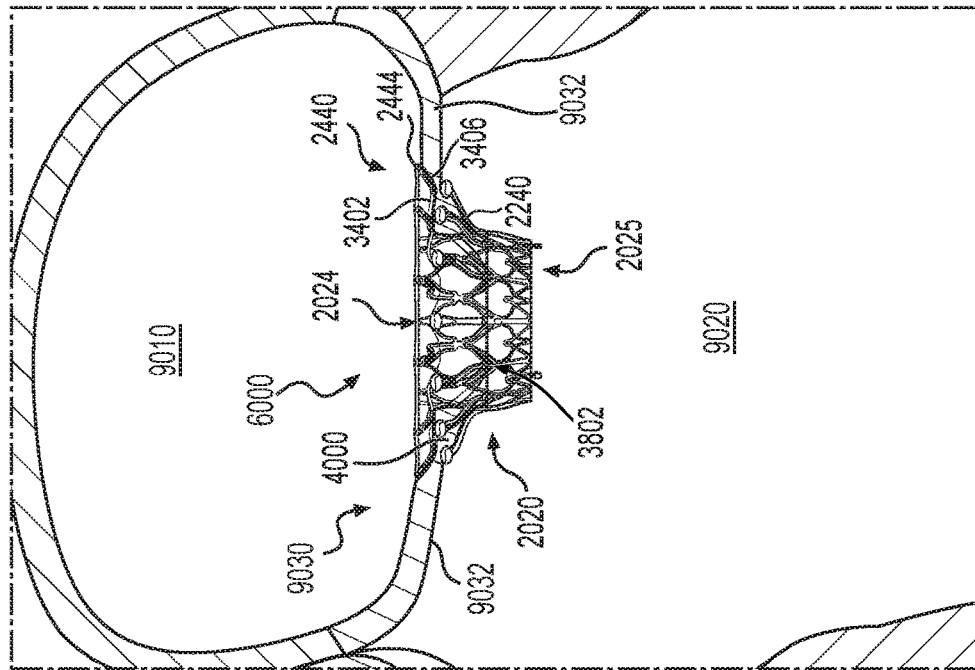
Figure 10G:
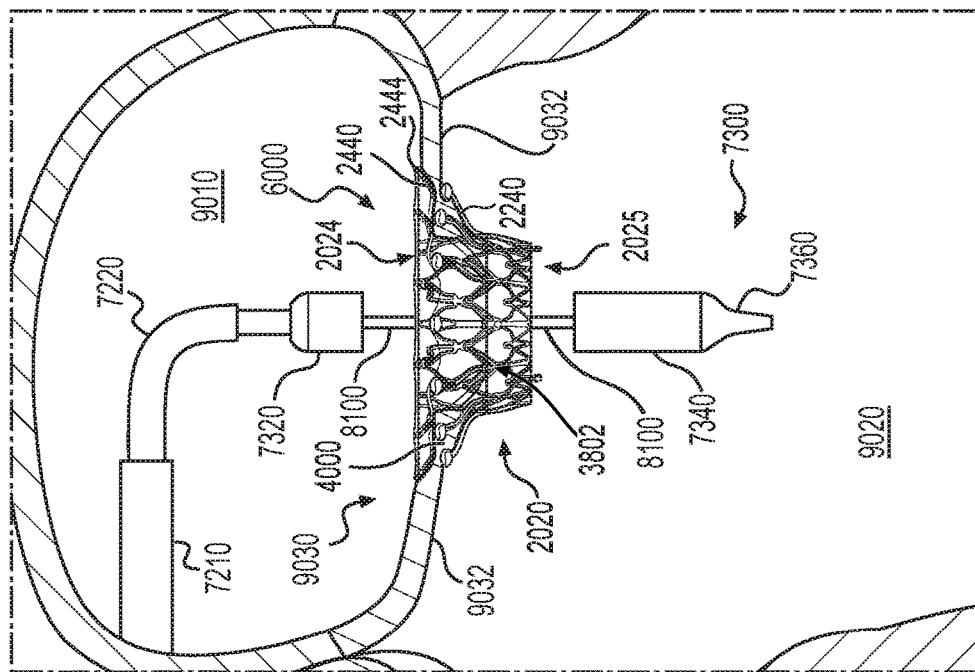

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valves, including prosthetic heart valves. While the present disclosure provides examples of prosthetic heart valves, and in particular prosthetic mitral valves, it should be noted that aspects of the disclosure in their broadest sense are not limited to a prosthetic mitral valve. Rather, the foregoing principles may be applied to other prosthetic valves as well. Prosthetic heart valve 6000, illustrated in FIGS. 6A-6E, is one example of a prosthetic valve in accordance with the present disclosure.

In some embodiments, a prosthetic valve may be configured for implantation at a treatment site within the body, such as within or adjacent to a native valve structure, such as a native mitral valve. In some embodiments, a prosthetic valve may be configured for transcatheter delivery to the implantation site via a variety of approaches, such as transapically, transatrially, and/or transseptally. In some embodiments, the prosthetic valve may be configured for implantation in the annulus or orifice of a native valve structure (e.g., a native mitral valve). For example, in FIGS. 10A-10H, prosthetic valve 6000 may be delivered to and expanded within native mitral valve 9030 such that prosthetic valve 6000 is anchored within native mitral valve 9030. In some embodiments, an exemplary prosthetic valve may be configured to grasp tissue of the native valve to firmly anchor the prosthetic valve within the native valve. For example, an exemplary prosthetic valve may be configured to grasp the native leaflets and/or native valve annulus to firmly seat the prosthetic valve within the valve annulus, thus preventing the prosthetic valve from migrating or dislodging from within the native valve annulus.

In some embodiments, an exemplary prosthetic valve may be configured for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting a ventricularly-directed force (that is, a force directed downwards toward ventricle 9020) upon atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

In some embodiments, the prosthetic valve may include an annular valve body. The exemplary annular valve body may be configured to receive or otherwise support a flow control device, such as one or more leaflets, for regulating flow of blood or other bodily fluids through the prosthetic valve. For example, the flow control device (e.g., leaflets) may be secured directly to the valve body and/or to an additional structure that is in turn secured to the valve body. As a result, when the prosthetic valve is implanted within a native valve (e.g., a mitral valve), the flow control device may regulate fluid passage through the native valve, thus restoring and/or replacing the functionality of the native valve. In some embodiments, the exemplary valve body may be annular or ring-shaped and may thus have at least one opening therein. In some embodiments, the at least one opening may extend longitudinally along the entire length of the annular valve body. For example, FIG. 2B illustrates an exemplary frame 2000 of a prosthetic heart valve. Heart valve frame 2000 may include an annular valve body 2020 having an axial lumen 2022 extending longitudinally therethrough. The annular valve body may be sized and configured to be seated within the orifice of a native mitral valve. For example, as depicted in FIG. 10H, annular valve body 2020 may be situated within the orifice of mitral valve 9030, specifically between native leaflets 9032. In some embodiments, the annular valve body may be configured to have a smaller diameter, when fully-expanded, than the diameter of the orifice of the native mitral valve. In such embodiments, the annular valve body may be anchored in the native mitral valve by anchoring structures, such as atrial anchoring arms and/or ventricular anchoring legs. Alternatively, the annular valve body may be configured to expand to an equal or greater diameter than the diameter of the mitral valve orifice such that the annular valve body is anchored within the mitral valve.

The annular valve body may have a circular, oval-shaped, elliptical, or D-shaped cross-section and may be symmetrical about at least one axis thereof. Alternatively, the annular valve body may have any suitable cross-sectional shape with at least one opening therein. In some embodiments, at least a portion of the annular valve body may be cylindrical, with a substantially constant diameter along the entire longitudinal length thereof. Alternatively, the annular valve body may have a variable diameter at different portions thereof (e.g., at different longitudinal portions thereof). Advantageously, such a configuration may improve the seating of the annular valve body within the mitral valve orifice, providing an improved pressure fit therebetween.

In some embodiments, the annular valve body may be expandable, such as between a radially-contracted configuration (e.g., a crimped state) and a radially-expanded configuration. The diameter of the annular valve body may be reduced when the annular valve body assumes the radially-contracted configuration; for example, the annular valve body may be arranged in the radially-contracted configuration when the exemplary prosthetic valve is delivered to the implantation site. Conversely, the diameter of the annular valve body may be increased when the annular valve body assumes the radially-expanded configuration. For example, the annular valve body may expand to its largest possible diameter when it is in the radially-expanded configuration.

In some embodiments, the annular valve body may be configured for self-expansion to the radially-expanded configuration; that is, the valve body may be biased to assume the radially-expanded configuration due to, at least in part, the design and/or material composition of the annular valve body. Additionally, or alternatively, the annular valve body may be configured to expand due to application of radially expansive forces thereupon.

In some embodiments, the annular valve body may include a plurality of supporting members or struts. In some embodiments, the struts may intersect at junctions to form a wire mesh, stent-like, or cage-like structure of the annular valve body. In some embodiments, the struts of the annular valve body may be made of metals or alloys such as Nitinol.

In some embodiments, the annular valve body may include an atrial end. In some embodiments, the atrial end may refer to a portion of the annular valve body configured to be situated closest to an atrium of the heart when the annular valve body is positioned outside of the atrium. Additionally, or alternatively, the atrial end may refer to a portion of the annular valve body configured to be situated at a location within the atrium that is furthest from an adjacent ventricle. For example, as depicted in FIG. 2A, atrial end inner frame junctions 3002 may constitute the atrial end 2024 of exemplary annular valve body 2020 because the atrial end inner frame junctions 3002 are the portions of annular valve body 2020 that are situated within atrium 9010 at a location furthest from ventricle 9020 (as shown in FIG. 10H).

In some embodiments, the annular valve body may include a ventricular end. In some embodiments, the ventricular end may refer to a portion of the annular valve body configured to be situated closest to a ventricle of the heart when the annular valve body is positioned outside of the ventricle. Additionally, or alternatively, the ventricular end may refer to a portion of the annular valve body configured to be situated at a location within the ventricle that is furthest from an adjacent atrium. For example, in some embodiments and as depicted in FIGS. 2A, 3A, and 3C, ventricular end inner frame junctions 3004 and ventricular end outer frame junctions 3604 may constitute the ventricular end 2025 of annular valve body 2020 because they are the portions of annular valve body 2020 that are situated within ventricle 9020 at a location furthest from atrium 9010 (as shown in FIG. 10H). In such embodiments, the ventricular end inner frame junctions 3004 (i.e., the exemplary ventricular end of inner frame 2400) and the ventricular end outer frame junctions 3604 (i.e., the exemplary ventricular end of outer frame 2200) may be evenly aligned within a plane perpendicular to longitudinal axis 2800. That is, the ventricular end inner frame junctions 3004 and the ventricular end outer frame junctions 3604 may be situated at the same axial position along longitudinal axis 2800. In some alternative embodiments, the ventricular end inner frame junctions 3004 may constitute the ventricular end 2025 of annular valve body 2020. In some further alternative embodiments, the ventricular end outer frame junctions 3604 may constitute the ventricular end 2025 of annular valve body 2020.

In some embodiments, the annular valve body may include an intermediate portion extending between the atrial end and ventricular end of the annular valve body. In some embodiments, the intermediate portion of the annular valve body may constitute every portion of the annular valve body situated in between the atrial end and ventricular end of the annular valve body. For example, as depicted in FIG. 2A, intermediate portion 2026 of annular valve body 2020 may include every portion of the annular valve body positioned between atrial end 2024 and ventricular end 2025.

In some embodiments, the exemplary prosthetic valve may include one or a plurality of tissue anchors. In some embodiments, the tissue anchors may be configured to anchor the prosthetic valve at the implantation site, such as within or near the native mitral valve. In some embodiments, the tissue anchors may be configured to engage ventricular tissue of the native mitral valve to anchor the prosthetic valve therein. In some embodiments, the tissue anchors may be configured to be positioned at least partially within a ventricle upon implantation of the prosthetic valve, and to engage ventricular tissue of the native mitral valve. For example, FIGS. 10E-10H depict ventricular anchoring legs 2240 of an exemplary prosthetic heart valve 6000. Ventricular anchoring legs 2240 are situated within ventricle 9020 and may engage the ventricular side of native mitral valve 9030 to secure prosthetic heart valve 6000 within the mitral valve; accordingly, ventricular anchoring legs 2240 may be considered tissue anchors in some embodiments.

In some embodiments, the tissue anchors may be configured to minimize or prevent migration of the prosthetic valve, including in an atrial direction (that is, towards the atrium), after the prosthetic valve is implanted. This may be due, at least in part, to the engagement of the tissue anchors with native tissue (e.g., the ventricular side of the native mitral valve) and the inability of the tissue anchors to pass through the mitral valve orifice after the prosthetic valve is implanted. For example, the tissue anchors may have sufficient length such that they may be configured to have a greater radius than the native mitral valve. Additionally, or alternatively, the tissue anchors may be configured to grasp or clamp tissue of the native mitral valve to further anchor the prosthetic valve in place. For example, in the embodiment of FIGS. 10G and 10H, ventricular anchoring legs 2240 (i.e., the exemplary tissue anchors) may clamp tissue by exerting an atrially-directed force (that is, a force directed towards atrium 9010) on the tissue, thus creating a sandwiching effect in coordination with atrial anchoring arms 2440, which may firmly anchor prosthetic heart valve 6000 within the mitral valve.

The prosthetic valve may include two tissue anchors, three tissue anchors, four tissue anchors, five tissue anchors, six tissue anchors, seven tissue anchors, eight tissue anchors, nine tissue anchors, ten tissue anchors, eleven tissue anchors, twelve tissue anchors, thirteen tissue anchors, fourteen tissue anchors, fifteen tissue anchors, sixteen tissue anchors, seventeen tissue anchors, eighteen tissue anchors, nineteen tissue anchors, twenty tissue anchors, or any other suitable number of tissue anchors. For example, exemplary prosthetic valve 6000 depicted in FIG. 2B may include twelve ventricular anchoring legs 2240 (i.e., the exemplary tissue anchors).

In some embodiments, the tissue anchors may be arranged about the annular valve body. The tissue anchors may be arranged at a regular interval about the annular valve body; alternatively, the tissue anchors may be arranged at some other interval about the annular valve body. In some embodiments, the tissue anchors may be arranged about a circumference of the annular valve body such that the tissue anchors may be evenly aligned within a plane perpendicular to longitudinal axis 2800; that is, the tissue anchors, or certain portions thereof, may be situated at the same axial position along longitudinal axis 2800. For example, in FIGS. 2A and 2B, ventricular anchoring legs 2240 (i.e., the exemplary tissue anchors) are arranged at a regular interval about annular valve body 2020. Anchoring legs 2240 (including, e.g., distal ends 2444 thereof), may be configured at a common axial position along axis 2800. In some alternative embodiments, the tissue anchors may be arranged in an alternative manner relative to the annular valve body. In some further alternative embodiments, the tissue anchors may be arranged at least partially within the annular valve body. In some further alternative embodiments, the tissue anchors may extend from the annular valve body at substantially similar heights. The distal ends of the tissue anchors may further extend to a substantially similar height above the point at which the tissue anchors extend from the annular valve body.

In some embodiments, the tissue anchors may be configured to extend from connection points on the annular valve body. In some embodiments, the connection points may refer to specific portions of the annular valve body to which the tissue anchors are connected to or otherwise secured. For example, in FIGS. 2A and 3A, ventricular anchoring legs 2240 (i.e., the exemplary tissue anchors) extend from leg attachment junctions 3802, which may be situated in an outer frame 2200 of the exemplary prosthetic valve. In some embodiments, the tissue anchors may be physically connected to the connection points on the annular valve body, such as by welding or adhesive. In some alternative embodiments, the tissue anchors may be integrally formed with the connection points on the annular valve body. In some embodiments, at least one tissue anchor may extend from a single connection point on the annular valve body. For example, in FIGS. 2A and 3A, each ventricular anchoring leg 2240 may extend from a single leg attachment junction 3802, with no two ventricular anchoring legs extending from the same leg attachment junction. Alternatively, at least one tissue anchor may extend from multiple connection points on the annular valve body.

In some embodiments, the exemplary prosthetic valve may include at least one protective fabric covering extending over each of the connection points between each tissue anchor and the valve body. The at least one protective fabric covering may refer to a particular material layer or textile configured to cover and protect at least a portion of the exemplary prosthetic valve. In some embodiments, the at least one protective fabric covering may be wrapped around at least a portion of the tissue anchors, including the connection points between the tissue anchors and the annular valve body, such that the connection points may be completely covered by the at least one protective fabric covering. For example, FIGS. 6A-6B depict protective coverings 6320, which are wrapped around the proximal ends of ventricular anchoring legs 2240 (i.e., the exemplary tissue anchors) and which contact first cuff sheet 6210 (which is arranged around annular valve body 2020 in an atrial direction from legs 2240) and skirt layer 6100 (which is arranged around annular valve body 2020 in a ventricular direction from legs 2240). As a result, protective coverings 6320 wrap around and completely cover leg attachment junctions 3802 (i.e., the exemplary connection points of legs 2240 to annular valve body 2020). In some alternative embodiments, at least one connection point between the tissue anchors and annular valve body may not be covered by the at least one protective fabric covering.

Advantageously, the at least one protective fabric covering may protect the connection points between the tissue anchors and annular valve body during and after the implantation process of the prosthetic valve. The at least one protective fabric covering may also protect native tissue from being injured by the connection point. For example, the protective fabric covering may protect tissue from injury resulting from being pinched between a tissue anchor and the annular valve body, both of which may be constructed of a rigid material such as Nitinol. The protective fabric covering may also protect tissue within the ventricle, including the chordae tendineae, from rubbing against and being injured by the connection point.

In some embodiments, each connection point between the tissue anchors and the annular valve body may be covered by a separate protective fabric covering. In some embodiments, the prosthetic valve may include the same number of protective fabric coverings as tissue anchors. Alternatively, the prosthetic valve may include a greater number of protective fabric coverings than tissue anchors. For example, prosthetic heart valve 6000 depicted in FIG. 6A may include distinct protective coverings 6320 extending over the leg attachment junctions 3802 of each ventricular anchoring leg 2240 (i.e., the exemplary tissue anchors). In some embodiments, each leg attachment junction 3802 may be covered by a single distinct protective covering 6320. Alternatively, at least one leg attachment junction 3802 may be covered by two or more protective coverings 6320. In some embodiments, the exemplary prosthetic valve may be devoid of protective fabric coverings extending between and contacting two or more connection points between tissue anchors and the annular valve body. For example, in the embodiment depicted in FIG. 6A, no individual protective fabric covering extends between and contacts multiple ventricular anchoring legs 2240 or their corresponding leg attachment junctions 3802.

In some embodiments, each of the at least one protective fabric coverings may cover less than half of a surface area of the corresponding tissue anchor. As used herein, the expression "surface area" may refer to the portions of the tissue anchors on the outer surface of the tissue anchors. As discussed above, the protective fabric coverings may extend around at least a portion of the tissue anchors (e.g., the protective fabric coverings may be wrapped around the tissue anchors). As a result, the surface area of the tissue anchors may be at least partially covered by the protective fabric coverings. However, each of the at least one protective fabric coverings may be configured to extend around the tissue anchors such that less than half of the surface area of each tissue anchor is covered by the protective fabric coverings. In some embodiments, each of the at least one protective fabric coverings may cover less than a quarter of the surface area of the corresponding tissue anchor. Alternatively, each of the at least one protective fabric coverings may cover less than a tenth of the surface area of the corresponding tissue anchor. Without limitation, for example, each of the at least one protective fabric coverings may cover less than 1%, 2%, 3%, 4%, 5%, 6%, 7%, 8%, 9%, 10%, 12.5%, 15%, 17.5%, 20%, 22.5%, 25%, 27.5%, 30%, 32.5%, 35%, 37.5%, 40%, 42.5%, 45%, 47.5%, 48%, 48.5%, 49%, 49.5%, or any other suitable portion of the corresponding tissue anchor.

In some embodiments, each of the at least one protective fabric covering may be arranged so as to expose a terminal end of the corresponding tissue anchor. That is, the protective fabric coverings may be arranged about the tissue anchors such that the distal, terminal ends of the tissue anchors are not covered by the protective fabric coverings. In some embodiments, the terminal ends of the tissue anchors may refer to the ends of the tissue anchors which are furthest from or most distal to the points of connection of the tissue anchors to the annular valve body. For example, FIGS. 6A-6B depict protective coverings 6320 configured to cover leg attachment junctions 3802 (i.e., the exemplary connection points of ventricular anchoring legs 2240 to annular valve body 2020). Protective coverings 6320 are also configured such that they do not cover the terminal ends of the ventricular anchoring legs 2240; instead, the terminal ends of the ventricular anchoring legs 2240 may be covered by a separate protective layer 6330. In some embodiments, the protective fabric coverings may cover the inner-most portions of the tissue anchors and may not extend beyond a midpoint between the proximal and distal ends of the tissue anchors. For example, as depicted in FIGS. 6A-6B, protective coverings 6320 are arranged about the inner-most portions of ventricular anchoring legs 2240 and do not cover any portion of the outer radial half of the ventricular anchoring legs.

In some embodiments, the at least one protective fabric covering may be at least partially constructed of a polymer such as polyethylene terephthalate (PET). In some embodiments, the entirety of at least one protective fabric covering may be constructed of PET. In some embodiments, at least one protective fabric covering may be at least partially constructed of a synthetic organic material, a synthetic polymer, a natural polymer, and/or a thermoplastic polymer such as a polycarbonate, a polyoxymethylene, an acrylic, a nylon, a polyethylene, a tetrafluoroethylene, a polypropylene, a polystyrene, a polyvinyl chloride, or a fluoropolymer.

In some embodiments, the at least one protective fabric covering may be secured relative to the annular valve body, at least in part, by stitching. In some embodiments, an additional securing mechanism, such as an adhesive, staples, rivets, or other suitable fasteners may be used in combination with stitching to secure the protective fabric coverings relative to the annular valve body. In some embodiments, portions of the protective fabric coverings may be stitched directly to the annular valve body. Additionally, or alternatively, portions of the protective fabric coverings may be stitched to an intermediate structure, such as a protective liner, which may in turn be secured to the annular valve body. In some embodiments, the stitching may pass through the protective fabric coverings to secure the coverings relative to the annular valve body. For example, in FIG. 6A, stitching 6322 passes through protective covering 6320 and skirt layer 6100 to secure them together. Skirt layer 6100 may, in turn, be secured to annular valve body 2020 (e.g., by stitching) such that protective covering 6320 is also secured to annular valve body 2020. Additionally, or alternatively, protective covering 6320 may be stitched to first cuff sheet 6210 and/or directly to annular valve body 2020, with the stitching passing through protective covering 6320.

In some embodiments, the stitching passing through the at least one protective fabric covering to secure the at least one protective fabric covering relative to the annular valve body may be configured to secure distinct portions of at least one protective fabric covering together. That is, for at least one protective fabric covering, separate portions of the covering may be secured together by the stitching. In some embodiments, at least one protective fabric covering may have an elongated structure (e.g., a rectangular structure) extending between two opposite ends of the protective fabric covering; the two opposite ends of the elongated structure may be secured together by the stitching. For example, protective coverings 6320 depicted in FIG. 6A may have an elongated structure (e.g., a rectangular structure) wrapped around ventricular anchoring legs 2240. Stitching 6322 may pass between the two ends of the elongated protective coverings 6320, one of which may be positioned over the other, thus securing the ends together and preventing the ends from becoming inadvertently dislodged.

In some embodiments, the prosthetic valve may include a skirt layer extending around at least a portion of the annular valve body. The skirt layer may cover the outer surface of at least a portion of the annular valve body; additionally, or alternatively, the skirt layer may cover the interior surface of at least a portion of the annular valve body. For example, as mentioned above, prosthetic valve 6000 illustrated in FIGS. 6A-6B includes a skirt layer 6100 extending around a portion of the outer surface of the annular valve body 2020. The skirt layer may be blood-impermeable such that it may be configured to prevent blood leakage between the inner and outer surfaces of the annular valve body, instead directing blood through a flow control device, such as one or more leaflets, situated within the annular valve body. FIGS. 6D and 6E, for example, illustrate prosthetic leaflets 6602, 6604, 6606 situated within exemplary annular valve body 2020.

The skirt layer may cover the ventricular end of the annular valve body and may extend along a portion of the axial length of the annular valve body. The skirt layer may be secured relative to the ventricular end of the annular valve body, such as by stitching, adhesive, staples, rivets, and/or any suitable fasteners. For example, as illustrated in FIGS. 6A-6C, skirt layer 6100 may be situated around ventricular end 2025 and may extend towards ventricular anchoring legs 2240 (i.e., the exemplary tissue anchors). In some embodiments, an atrial edge of skirt layer 6100 (that is, the top edge of skirt layer 6100 in FIG. 6A) may extend between the locations where ventricular anchoring legs 2240 are connected to annular valve body 2020.

The skirt layer may be connected to the annular valve body, for example, by stitching, adhesive, staples, rivets, and/or any suitable fasteners. In some embodiments, the skirt layer may be at least partially constructed of a fabric that is impermeable to blood but which may be configured to allow for tissue ingrowth. For example, the skirt layer may be constructed of at least one synthetic material, such as polyester material or a biocompatible polymer. Examples of a polyester material may include polyethylene terephthalate (PET) and expanded polytetrafluoroethylene (ePTFE), either alone, or in combination with at least one additional material. In some alternative embodiments, the skirt layer may be at least partially constructed of a biological material, such as pericardial tissue (e.g., bovine, porcine, or equine pericardium) or other biological tissue.

The skirt layer may be positioned beneath the at least one protective fabric covering; that is, the protective fabric covering may be situated over the skirt layer. In some embodiments, the stitching passing through the at least one protective fabric covering to secure the at least one protective fabric covering relative to the annular valve body may secure at least a portion of the at least one protective fabric covering to the skirt layer. For example, the stitching may pass through the protective fabric covering and portions of the skirt layer situated beneath and/or immediately adjacent to the protective fabric covering, thus securing the protective fabric covering and skirt layer together. For example, in FIG. 6A, stitching 6322 may pass through protective covering 6320 and skirt layer 6100, thus securing the protective covering and skirt layer together. Optionally, an additional securing mechanism, such as an adhesive, may be used in combination with stitching to secure the protective fabric covering to the skirt layer.

In some embodiments, the exemplary prosthetic valve may include a liner configured to cover a majority of a surface area of one or more of the tissue anchors. In some embodiments, a majority of a surface area of one or more of the tissue anchors may refer to more than half of the surface area of the one or more tissue anchors. Without limitation, for example, the liner may be configured to cover at least 51%, 60%, 70%, 80%, 90%, 91%, 92%, 93%, 94%, 95%, 96%, 97%, 98%, 98%, 99%, 100%, or any other suitable portion of the surface area of the one or more the tissue anchors. In some embodiments, the liner may be configured to cover the entire surface area of one or more of the tissue anchors. In some embodiments, each tissue anchor may be at least partially covered by a separate liner. Alternatively, one liner may cover the majority of a surface area of at least two tissue anchors. For example, in FIGS. 6A-6B, at least the majority of the surface area of ventricular anchoring legs 2240 (i.e., the exemplary tissue anchors) is covered by a ventricular anchoring leg liner 6310. In some embodiments, each liner 6310 may be a separate and distinct structure from the other liners 6310. In some embodiments, liners 6310 may be an extension of skirt layer 6100 such that a single, unitary liner may cover the majority of the surface areas of the ventricular anchoring legs.

In some embodiments, the at least one protective fabric covering may be positioned, at least partially, over the liner covering the tissue anchors. For example, as illustrated in FIG. 6B, protective coverings 6320 may be positioned over ventricular anchoring leg liners 6310. That is, coverings 6320 may be wrapped over liners 6310, covering a portion of liners 6310. Optionally, protective coverings 6320 may be stitched or otherwise connected to ventricular anchoring leg liners 6310 such that they may be secured together.

In some exemplary embodiments, at least two of the connection points between the tissue anchors and the annular valve body may be covered by separate protective fabric coverings. For example, all of the connection points between the tissue anchors and the annular valve body may be covered by separate protective fabric coverings. In such embodiments, the separate protective fabric coverings may be substantially aligned in a common plane. That is, the protective fabric coverings may be arranged within a common planar surface. For example, the separate protective fabric coverings may be substantially aligned in a common lateral plane. That is, the protective fabric coverings may be arranged within a plane substantially perpendicular to a longitudinal axis of the prosthetic valve. As a result, the protective fabric coverings may be configured at a common axial position along the longitudinal axis. For example, in FIG. 6A, protective coverings 6320 are substantially aligned in a common lateral plane, such that they are configured at a common axial position along longitudinal axis 2800. For example, protective coverings 6320 may be equidistant from the atrial end of the annular valve body and/or from the ventricular end of the annular valve body.

In some embodiments, at least one protective fabric covering may be positioned in a radially outer direction relative to the annular valve body. That is, the at least one protective fabric covering may be positioned exterior to the annular valve body, and at a greater distance from the longitudinal axis of the prosthetic valve than is the annular valve body. In some embodiments, the entirety of the at least one protective fabric covering may be positioned in a radially outer direction relative to the annular valve body. Alternatively, a portion of the at least one protective fabric covering may be positioned in a radially outer direction relative to the annular valve body. This may be achieved, for example, because the at least one protective fabric covering may be arranged along an exterior surface of the annular valve body. Alternatively, the at least one protective fabric covering may be positioned on an element (e.g., a tissue anchor) which may extend radially outwards from the annular valve body, thus positioning the at least one protective fabric covering in a radially outward direction from the annular valve body. For example, in FIG. 6B, protective coverings 6320 are positioned in a radially outer direction relative to at least a portion of the annular valve body 2020. In some embodiments, protective coverings 6320 may be positioned in a radially outer direction relative to the entire axial length of the annular valve body 2020. In some alternative embodiments, at least a portion of one or more protective fabric covering may be positioned in a radially inner direction relative to the annular valve body.

In some embodiments, the plurality of tissue anchors may be configured to expand between a radially-contracted configuration (such as a crimped state) and a radially-expanded configuration. The tissue anchors, including their respective terminal ends, may be situated closer to the longitudinal axis of the prosthetic valve when the tissue anchors are in the radially-contracted configuration compared to when the tissue anchors are in the radially-expanded configuration. In some embodiments, the tissue anchors may be configured to lie adjacent to, or flush with, a portion of the annular valve when the tissue anchors are in the radially-contracted configuration, and to deflect away from the annular valve when the tissue anchors are in the radially-expanded configuration. For example, FIG. 5A depicts a plurality of ventricular anchoring legs 2240 (i.e., the exemplary tissue anchors) in a radially-contracted configuration, in which they are flush with annular valve body 2020. FIG. 5B illustrates ventricular anchoring legs 2240 in a radially-expanded configuration, in which the terminal ends 2244 of the legs deflect away from annular valve body 2020. FIG. 5E also illustrates ventricular anchoring legs 2240 in the radially-expanded configuration, with annular valve body 2020 also in its radially-expanded configuration.

In some embodiments, the tissue anchors may have shape memory such that they are configured for self-expansion to the radially-expanded configuration. For example, the tissue anchors may be constructed of a shape memory material such as Nitinol and may be constructed to be biased towards the radially-expanded configuration. Additionally, or alternatively, the tissue anchors may be configured to expand to the radially-expanded configuration due to application of radially expansive forces thereupon.

In some embodiments, the at least one protective fabric covering may be arranged so as not to impede movement of the tissue anchors from the radially-contracted configuration to the radially-expanded configuration. That is, the tissue anchors may be configured to expand from the radially-contracted configuration to the radially-expanded configuration without interference from the at least one protective fabric covering. For example, the at least one protective fabric covering may be devoid of connections to the portions of the annular valve body which the tissue anchors deflect away from when the tissue anchors expand to the radially-expanded configuration. Thus, when the tissue anchors expand to the radially-expanded configuration, the at least one protective fabric covering may not create a connection between the tissue anchors and the valve body which would prevent tissue anchor expansion. Additionally, or alternatively, the at least one protective fabric covering may be sufficiently pliant so as to accommodate structural changes in the tissue anchor during radial expansion thereof.

In some embodiments, the at least one protective fabric covering may include a single strip of fabric wrapped about the connection point between the corresponding tissue anchor and the annular valve body. For example, the strip of fabric may be elongated between two opposite ends, and the strip may be wrapped about the at least one connection point such that one of the opposite ends is positioned over the other. For example, FIG. 6A depicts protective coverings 6320 as strips of fabric wrapped around the proximal ends of ventricular anchoring legs 2240 (i.e., the exemplary tissue anchors) and the connection points between the legs 2240 and the annular valve body 2020. In some embodiments, at least one protective fabric covering may include multiple strips of fabric wrapped about the corresponding connection point.

In some embodiments, a terminal end of at least one tissue anchor may be configured to be situated in an atrial direction relative to the at least one protective fabric covering. In some embodiments, the terminal end of at least one tissue anchor may be configured to be situated in an atrial direction relative to the protective fabric covering associated with the tissue anchor. Additionally, or alternatively, the terminal end of at least one tissue anchor may be configured to be situated in an atrial direction relative to protective fabric coverings of at least one other tissue anchors. The terminal end of the at least one tissue anchor may be configured to be situated in an atrial direction relative to the protective fabric covering when the tissue anchor is in the radially-contracted configuration. Additionally, or alternatively, the terminal end of the at least one tissue anchor may be configured to be situated in an atrial direction relative to the protective fabric covering when the tissue anchor is in the radially-expanded configuration. For example, FIG. 6A illustrates an embodiment in which ventricular anchoring legs 2240 (i.e., the exemplary tissue anchors) are in a radially-expanded configuration. In the example of FIG. 6A, the terminal ends 2244 of the ventricular anchoring legs 2240 are situated in an atrial direction relative to the protective coverings 6320 (that is, terminal ends 2244 are upwards from protective coverings 6320 in FIG. 6A).

As discussed above, the exemplary prosthetic valve may include a plurality of leaflets situated within the annular valve body in some embodiments. FIG. 6D, for example, illustrates prosthetic leaflets 6602, 6604, 6606 situated within lumen 2022 of annular valve body 2020. The prosthetic valve may include two leaflets, three leaflets, four leaflets, or any other suitable number of leaflets. The leaflets may be constructed of various suitable materials, such as natural tissue (e.g., bovine pericardial tissue) or synthetic materials. The leaflets may be configured to function in a manner similar to the leaflets of the native mitral valve. For example, the leaflets may be configured to assume an open position (e.g., FIG. 6D), in which a space is formed between the leaflets, allowing blood and other fluids to pass. The leaflets may also be configured to assume a closed position (e.g., FIG. 6E), in which the leaflets may coapt with one another so as to prevent fluid passage between the leaflets. The leaflets may function as a one way valve, such that flow in one direction (e.g., from the atrium to the ventricle) opens the valve and flow in a second, opposite direction (e.g., from the ventricle to the atrium) closes the valve. In some embodiments, the leaflets may be configured to open during diastole and close during systole.

In some embodiments, the leaflets may be connected to certain portions of the annular valve body. For example, the atrial ends of the leaflets may be connected to the annular valve body or to an intermediate structure (e.g., a liner) which may, in turn, be connected to the annular valve body. The leaflets may be connected to the annular valve body and/or to the intermediate structure by stitching, adhesive, staples, rivets, and/or any suitable fasteners. For example, in FIGS. 6D and 6E, leaflets 6602, 6604, and 6606 are connected, along their respective atrial ends, to inner liner 6400, which may be situated at least in part within the central lumen of annular valve body 2020. Leaflets 6602, 6604, and 6606 may be connected to inner liner 6400 via stitching 6608 and/or by any suitable fastening means. Inner liner 6400 may, in turn, be connected to the annular valve body 2020, thus securing the leaflets to the annular valve body. Additionally, or alternatively, the ventricular ends of the leaflets may be connected to the annular valve body or to an intermediate structure (e.g., a liner) which may, in turn, be connected to the annular valve body. For example, as illustrated in FIG. 6C, leaflets 6602, 6604 (as well as leaflet 6606, which is not depicted in FIG. 6C) may be connected to ventricular end delivery post 2028, such as by stitching 6610 which may loop around the delivery post 2028 to secure the leaflets to the annular valve body 2020. As illustrated in FIG. 6A, delivery post 2028 may be situated in a ventricular direction relative to protective coverings 6320. Accordingly, a point of connection between the leaflets and the annular valve body (e.g., the connection between leaflets 6602, 6604, 6606 and delivery post 2028) may be situated in a ventricular direction relative to the at least one protective fabric covering.

In some embodiments, the exemplary tissue anchors of the prosthetic valve may be configured to engage ventricular tissue of a native heart valve, so as to anchor the prosthetic valve within the native heart valve. For example, the tissue anchors may be configured to contact the ventricular surface of the native heart valve, so as to prevent migration of the prosthetic valve in an atrial direction. Additionally, or alternatively, the tissue anchors may be configured to grasp or clamp tissue of the native heart valve to further anchor the prosthetic valve in place. For example, FIGS. 10E-10H depict ventricular anchoring legs 2240 (i.e., the exemplary tissue anchors) situated within ventricle 9020. Ventricular anchoring legs 2240 may engage the ventricular side of native mitral valve 9030 to secure prosthetic heart valve 6000 within the mitral valve.

In some embodiments, the exemplary prosthetic valve may additionally include a plurality of atrial tissue anchors. In some embodiments, the atrial tissue anchors may be configured to engage atrial tissue of the native mitral valve to anchor the prosthetic valve therein. In some embodiments, the atrial tissue anchors may be configured to be positioned at least partially within an atrium upon implantation of the prosthetic valve, and to engage atrial tissue of the native mitral valve. For example, FIGS. 10F-10H depict atrial anchoring arms 2440 of an exemplary prosthetic heart valve 6000. Atrial anchoring arms 2440 are situated within atrium 9010 and may engage the atrial side of native mitral valve 9030 to secure prosthetic heart valve 6000 within the mitral valve; accordingly, atrial anchoring arms 2440 may be considered atrial tissue anchors in some embodiments.

In some embodiments, the atrial tissue anchors may be configured to minimize or prevent migration of the prosthetic valve, including in a ventricular direction (that is, towards the ventricle), after the prosthetic valve is implanted. This may be due, at least in part, to the engagement of the atrial tissue anchors with native tissue (e.g., the atrial side of the native mitral valve) and the inability of the atrial tissue anchors to pass through the mitral valve orifice after the prosthetic valve is implanted. For example, the atrial tissue anchors may have sufficient length such that they may be configured to have a greater radius than the native mitral valve. Additionally, or alternatively, the atrial tissue anchors may be configured to grasp or clamp tissue of the native mitral valve to further anchor the prosthetic valve in place. For example, in the embodiment of FIGS. 10G and 10H, atrial anchoring arms 2440 (i.e., the exemplary atrial tissue anchors) may clamp tissue by exerting a ventricularly-directed force (that is, a force directed towards ventricle 9020) on the tissue, thus creating a sandwiching effect in coordination with ventricular anchoring legs 2240 which may firmly anchor prosthetic heart valve 6000 within the mitral valve.

The prosthetic valve may include two atrial tissue anchors, three atrial tissue anchors, four atrial tissue anchors, five atrial tissue anchors, six atrial tissue anchors, seven atrial tissue anchors, eight atrial tissue anchors, nine atrial tissue anchors, ten atrial tissue anchors, eleven atrial tissue anchors, twelve atrial tissue anchors, thirteen atrial tissue anchors, fourteen atrial tissue anchors, fifteen atrial tissue anchors, sixteen atrial tissue anchors, seventeen atrial tissue anchors, eighteen atrial tissue anchors, nineteen atrial tissue anchors, twenty atrial tissue anchors, or any other suitable number of atrial tissue anchors. For example, exemplary prosthetic valve 6000 depicted in FIG. 2B may include twelve atrial anchoring arms 2440 (i.e., the exemplary atrial tissue anchors).

In some embodiments, the annular valve body may include one or more frames. In some embodiments, the annular valve body may include an outer frame and an inner frame situated at least partially within the outer frame. In some embodiments, one or both of the inner frame and the outer frame may be annular, and the inner frame may be positioned within an opening of the outer frame. For example, FIG. 2A depicts an exemplary prosthetic valve frame 2000 having an outer frame 2200 and an inner frame 2400. In some alternative embodiments, the inner frame may be situated entirely within the outer frame. One or both of the inner frame and the outer frame may be configured to radially expand between a radially-contracted configuration (e.g., a crimped state) and a radially-expanded configuration. In some embodiments, the inner frame may be configured to receive or otherwise support a flow control device, such as one or more leaflets, for regulating flow of blood or other bodily fluids through the prosthetic valve.

In some embodiments, the exemplary ventricular tissue anchors may be configured to extend from the annular outer frame. Additionally, or alternatively, the exemplary atrial tissue anchors may be configured to extend from the inner frame. For example, FIG. 3A depicts atrial anchoring arms 2440 (i.e., the exemplary atrial tissue anchors) extending from inner frame 2400, and FIG. 3C depicts ventricular anchoring legs 2240 (i.e., the exemplary ventricular tissue anchors) extending from outer frame 2200. In some embodiments, the atrial tissue anchors and the ventricular tissue anchors may be physically connected to the inner frame and annular outer frame, respectively, such as by welding or adhesive. In some alternative embodiments, the atrial tissue anchors and the ventricular tissue anchors may be integrally formed with the inner frame and annular outer frame, respectively.

In some embodiments, the at least one protective fabric covering may be positioned in a radially outer direction relative to the inner frame and annular outer frame. That is, the at least one protective fabric covering may be positioned exterior to both the inner frame and annular outer frame, and at a greater distance from the longitudinal axis of the prosthetic valve than are the inner frame and annular outer frame. In some embodiments, the entirety of the at least one protective fabric covering may be positioned in a radially outer direction relative to the inner frame and annular outer frame. Alternatively, a portion of the at least one protective fabric covering may be positioned in a radially outer direction relative to the inner frame and annular outer frame. This may be achieved, for example, because the at least one protective fabric covering may be arranged along an exterior surface of the annular outer frame, which may in turn be situated in a radially outer direction relative to the inner frame. Alternatively, the at least one protective fabric covering may be positioned on an element (e.g., a ventricular tissue anchor) which may extend radially outward from the inner frame and annular outer frame, thus positioning the at least one protective fabric covering in a radially outward direction from the inner frame and annular outer frame. For example, in FIG. 6B, protective coverings 6320 are positioned in a radially outer direction relative to at least a portion of annular outer frame 2200 and relative to at least a portion of inner frame 2400. In some embodiments, protective coverings 6320 may be positioned in a radially outer direction relative to the entire axial length of one or both of the annular outer frame 2200 and inner frame 2400. In some alternative embodiments, at least a portion of one or more protective fabric covering may be positioned in a radially inner direction relative to the inner frame and annular outer frame.

In some embodiments, the at least one protective fabric covering may be situated in a ventricular direction relative to the atrial tissue anchors. In some embodiments, the at least one protective fabric covering may be situated in a ventricular direction relative to some or all of the atrial tissue anchors. The at least one protective fabric covering may be situated in a ventricular direction relative to the atrial tissue anchors when the atrial tissue anchors are in a radially-contracted configuration. Additionally, or alternatively, the at least one protective fabric covering may be situated in a ventricular direction relative to the atrial tissue anchors when the atrial tissue anchors are in a radially-expanded configuration. For example, FIG. 6A illustrates an embodiment in which atrial anchoring arms 2440 (i.e., the exemplary atrial tissue anchors) are in a radially-expanded configuration. In the example of FIG. 6A, protective coverings 6320 are situated in a ventricular direction relative to the atrial anchoring arms 2440, including the proximal arm end 3020 and the distal arm end 2444.

In some embodiments, the atrial tissue anchors and ventricular tissue anchors may be angularly offset from each other, relative to the longitudinal axis of the prosthetic valve. That is, the atrial tissue anchors and ventricular tissue anchors may be situated at different positions about the circumference of the annular valve body. Because the at least one protective fabric covering may cover a portion of the ventricular tissue anchors, it follows that the at least one protective fabric covering is also angularly offset from the atrial tissue anchors. In some embodiments, the protective fabric coverings and atrial tissue anchors may be spaced at a regular interval about the circumference of the annular valve body. Alternatively, the protective fabric coverings and atrial tissue anchors may be spaced at another pattern about the circumference of the annular valve body. For example, in FIG. 6A, protective coverings 6320 are angularly offset at a regular interval from atrial anchoring arms 2440 (i.e., the exemplary atrial tissue anchors).

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A prosthetic valve for implantation within a native mitral valve, the prosthetic valve comprising:
   an annular valve body;
   a plurality of tissue anchors arranged about the valve body and configured to extend from connection points on the valve body; and
   at least one protective fabric covering extending over each of the connection points between each tissue anchor and the valve body; wherein:
      each connection point is covered by a separate protective fabric covering; and
      each of the at least one protective fabric covering covers less than half of a surface area of the corresponding tissue anchor.

2. The prosthetic valve of claim 1, wherein the at least one protective fabric covering is at least partially constructed of PET.

3. The prosthetic valve of claim 1, wherein stitching passes through the at least one protective fabric covering to secure the at least one protective fabric covering relative to the annular valve body.

4. The prosthetic valve of claim 3, wherein the stitching is configured:
   to secure distinct portions of the at least one protective fabric covering together, and
   to secure a portion of the at least one protective fabric covering to a skirt layer positioned beneath the at least one protective fabric covering.

5. The prosthetic valve of claim 1, wherein at least two of the connection points are covered by separate protective fabric coverings which are substantially aligned in a common plane.

6. The prosthetic valve of claim 5, wherein the separate protective fabric coverings are substantially aligned in a common lateral plane.

7. The prosthetic valve of claim 1, wherein the at least one protective fabric covering is positioned in a radially outer direction relative to the annular valve body.

8. The prosthetic valve of claim 1,
   wherein the plurality of tissue anchors are configured to expand from a radially-contracted configuration to a radially-expanded configuration, and
   wherein the at least one protective fabric covering is arranged so that the at least one protective fabric covering does not impede movement of the plurality of tissue anchors from the radially-contracted configuration to the radially-expanded configuration.

9. The prosthetic valve of claim 1, wherein a terminal end of at least one tissue anchor is configured to be situated in an atrial direction relative to the at least one protective fabric covering.

10. The prosthetic valve of claim 1, further comprising:
    a plurality of leaflets situated within the annular valve body,
    wherein a point of connection of the plurality of leaflets to the annular valve body is situated in a ventricular direction relative to the at least one protective fabric covering.

11. A prosthetic valve for implantation within a native mitral valve, the prosthetic valve comprising:
    an annular valve body;
    a plurality of tissue anchors arranged about the valve body and configured to extend from connection points on the valve body; and
    at least one protective fabric covering extending over each of the connection points between each tissue anchor and the valve body; wherein:
       each connection point is covered by a separate protective fabric covering; and
       each of the at least one protective fabric covering is arranged to expose a terminal end of the corresponding tissue anchor.

12. A prosthetic valve for implantation within a native mitral valve, the prosthetic valve comprising:
    an annular valve body;
    a plurality of tissue anchors arranged about the valve body and configured to extend from connection points on the valve body; and
    at least one protective fabric covering extending over each of the connection points between each tissue anchor and the valve body;
    wherein the at least one protective fabric covering is positioned over a liner which covers a majority of a surface area of one or more of the tissue anchors.

13. A prosthetic valve for implantation within a native mitral valve, the prosthetic valve comprising:
    an annular valve body;
    a plurality of tissue anchors arranged about the valve body and configured to extend from connection points on the valve body; and
    at least one protective fabric covering extending over each of the connection points between each tissue anchor and the valve body;
    wherein the at least one protective fabric covering includes a single strip of fabric wrapped about the at least one connection point.

14. A prosthetic valve for implantation within a native mitral valve, the prosthetic valve comprising:
    an annular valve body;
    a plurality of tissue anchors arranged about the valve body and configured to extend from connection points on the valve body; and
    at least one protective fabric covering extending over each of the connection points between each tissue anchor and the valve body; wherein:
       the tissue anchors are configured to engage ventricular tissue of a native heart valve;
       the prosthetic valve further comprises a plurality of atrial tissue anchors configured to engage atrial tissue of the native heart valve;
       the annular valve body includes an annular outer frame and an inner frame situated at least partially within the annular outer frame; and
       the ventricular tissue anchors extend from the annular outer frame and the atrial tissue anchors extend from the inner frame.

15. The prosthetic valve of claim 14, wherein the at least one protective fabric covering is positioned in a radially outer direction relative to the annular outer frame and relative to the inner frame.

16. The prosthetic valve of claim 14, wherein the at least one protective fabric covering is situated in a ventricular direction relative to the atrial tissue anchors.

17. The prosthetic valve of claim 14, wherein the at least one protective fabric covering is angularly offset from the atrial tissue anchors.

\* \* \* \* \*